United States Patent
Chiozza et al.

(10) Patent No.: US 11,965,169 B2
(45) Date of Patent: Apr. 23, 2024

(54) TRANSGENIC SAFFLOWER EVENT STACK IND-1ØØØ3-4 X IND-1ØØ15-7 AND METHODS TO USE IT

(71) Applicant: AG Biomolecules LLC, Wilmington, DE (US)

(72) Inventors: Mariana Chiozza, Ames, IA (US); Carlos Dezar, Paraná (AR); Patricia Miranda, Rosario (AR); Lucas Paultroni, Rosario (AR); Martin Salinas, Rosario (AR)

(73) Assignee: AG BIOMOLECULES LLC, Wilmington, DE (US)

( * ) Notice: Subject to any disclaimer, the term of this patent is extended or adjusted under 35 U.S.C. 154(b) by 239 days.

(21) Appl. No.: 16/998,742

(22) Filed: Aug. 20, 2020

(65) Prior Publication Data

US 2022/0056463 A1 Feb. 24, 2022

(51) Int. Cl.
*C12Q 1/6895* (2018.01)
*C12N 15/82* (2006.01)

(52) U.S. Cl.
CPC ....... *C12N 15/8257* (2013.01); *C12Q 1/6895* (2013.01); *C12Q 2600/13* (2013.01)

(58) Field of Classification Search
CPC .............. C12N 15/8257; C12Q 1/6895; C12Q 2600/13
See application file for complete search history.

(56) References Cited

U.S. PATENT DOCUMENTS 7,390,936 B1 * 6/2008 Van Rooijen et al. ............... C12N 15/8257 435/468
11,266,151 B2 3/2022 Bowen

OTHER PUBLICATIONS

Patial et al. "Development of an efficient, genotype independent plant regeneration and transformation protocol using cotyledonary nodes in safflower (*Carthamus tinctorius* L.)" 2016 J. Plant Biochem. Biotechnol. 25(4):421-432. (Year: 2016).*

(Continued)

*Primary Examiner* — Matthew R Keogh
*Assistant Examiner* — Rebecca Stephens
(74) *Attorney, Agent, or Firm* — Crowell & Moring LLP

(57) ABSTRACT

The present invention relates to a safflower plant or part thereof involving the molecular stacking of safflower events IND-1ØØØ3-4×IND-1ØØ15-7, wherein the plant produces and accumulates chymosin in seed under agricultural conditions. A plant seed involving the molecular stacking of safflower events IND-1ØØØ3-4×IND-1ØØ15-7. A consumer product produced from the seed, defined as chymosin, and additionally as ground grain, flour, flakes, oil, biodiesel, biogas, or another biomaterial.

Also, the present invention include a recombinant DNA molecule involved in the molecular stacking of safflower events IND-1ØØØ3-4×IND-1ØØ15-7. A DNA polynucleotide primer molecule comprising at least 15 contiguous nucleotides of the DNA molecule involved in the molecular stacking of safflower events IND-1ØØØ3-4×IND-1ØØ15-7, or its complement which is useful in a DNA amplification method to produce a diagnostic amplicon for the event IND-1ØØØ3-4 and IND-1ØØ15-7, or each of them separately IND-1ØØØ3-4 and IND-1ØØ15-7. A vector of functional expression in plants and the microorganism that comprises it. A DNA detection kit comprising at least one DNA molecule comprising a nucleotide sequence with a sufficient length of contiguous nucleotides of the recombinant DNA molecule involved in the molecular stacking of safflower events IND-1ØØØ3-4×IND-1ØØ15-7.

Furthermore, the present invention involves methods of producing a safflower plant that accumulates chymosin in seeds under agricultural conditions; methods of producing a chymosin-producing safflower plant; methods to detect the presence of DNA corresponding to the molecular stack of (Continued)

safflower events IND-1∅∅∅3-4×IND-1∅∅15-7, or each of them separately IND-1∅∅∅3-4 and IND-1∅∅15-7; methods for determining the zygosity of the safflower genome containing DNA from the molecular stack of safflower events IND-1∅∅∅3-4×IND-1∅∅15-7, or each of them separately IND-1∅∅∅3-4 or IND-1∅∅15-7; and methods of producing a consumer product made from safflower.

5 Claims, 11 Drawing Sheets

Specification includes a Sequence Listing.

(56) References Cited

OTHER PUBLICATIONS

Pollock et al. abstract BIOT 308 for poster at the 232nd ACS National Meeting held Sep. 10-14, 2006 in San Francisco, California; entitled "Production and pilot scale recovery of bovine chymosin B from safflower seed" (1 total page). (Year: 2006).*

Ying et al. "Agrobacterium tumefaciens-mediated transformation of safflower (*Carthamus tinctorius* L.) cv. 'Centennial'" 1992 Plant Cell Reports 11:581-585. (Year: 1992).*

Knowles and Ashri "Wild Safflower in California: improvement of cultivated safflower through plant-breeding program to obtain desirable characteristics of wild species" Apr. 1958 California Agriculture (2 total pages). (Year: 1958).*

U.S. Office Action received in U.S. Appl. No. 17/948,381 dated Jun. 29, 2023 (21 pages).

Mayerhofer, M., et al., "Introgression potential between safflower (*Carthamus tinctorius*) and wild relatives of the genus *Carthamus,*" *BMC Plant Biology*, 11(47):1-10 (2011).

GenBank Accession No GS895965.1 (version 1 dated Feb. 9, 2014, entitled "SAX3D05 Flanking Sequence Tag of *Oryza sativa* T-DNA insertion lines *Oryza sativa jagonic* Group genomic, genomic survey seguence," 2 pages (2014).

GenBank Accession No. J01263.1 (version 1 dated Jun. 17, 1998, entitled "Phaseolus vulgaris beta-type phaseolin storage protein gene, complete cds," 3 pages (1998).

* cited by examiner

SAFFLOWER TRANSGENIC EVENT IND-10003-4 X IND-10015-7

FIG. 7A (SEQ ID NOs: 21 and 22)

TTAAAAACAAGCTCCTTCCATGTATGAAAAAAACTTCTCAAGCTATACAGACACA
GATTAATCCACACAAACAACTTTATCCATACATGACTTGGAAAATCTTAGAGACGGA
TATATGTTCAAGAACATTACCAGCCAAACACTGATAGTTTAAACTGAAGGCGGGAAACGACAATCTGATCCAA
GCTCAAGCTGCTCTGTAGCATTGGCCATTCAGGCTGCGCAACTGTTGGGAAGGGGCGATCGGTGCGGGCCTCTTCG
CTATTACGCCAGCTGGCGAAAGGGGATGTGCTGCAAGGGCGATTAAGTTGGGTAACGCCAGGTTTCCCAGT
CACGACGTTGTAAAACGACGGCCAGTGCCAA

FIG. 7B (SEQ ID NOs: 23 and 24)

ATTAGGGTTCCTATAGGGTTTCGCTCATGTGTTGAGCATATAAGAAACCCTAGTATGTATTTGTATTTGTAA
AATACTTCTATCAATAAAATTTCTAATTCCTAAAACCAAATGTGTTATTAATCCAGATCCCCGAATTAA
TTCGGGTTAATTCAGTACATTAAAAACGTCGCAATGTGTTATTAAGTTGTCTAAGGCTAGGAAGCTTACG
ATTGGCCCTTTGCCAGATTCCGATCAAGCTCACTATCAGTCGAACGGTTCGAACATGAAACAATGCAAAGTA
ATCCCAATCGATCCACCTTGTTTACGCTGCACAGAGAAACCCAAATTAAACTATGAACAATATTTTCTTCAC
CAACGTGCAAAAGTACATCCAATCCAACAATG

FIG. 7C (SEQ ID NOs: 25 and 26)

CAGCAATGCAATGTATAGAAAGTCCCGTTTGTTAGCAACTTAATGAGCTTAATAGGACTGAGAACTTAT
TCGGTCAGCTATAAATGACTGTGTGGCTTGATGATATTGAAAGTGACTTATTCGTTAAGATTTACG
GGGGAGCTTTATGCAGAAATCCACAGAGTGCAACCAGTGCCATGGCAACCAGTAATTCCAGTTACGACTTACATACCA
AGAAAAGGTAAAGCAATAAGAACATTACTACTTTAAACTCTAAAACAATTTAAACATAGTAGAAT
ACACTCTAACACTCTAAACTCTAACATTACTTACTTTAAACTCTATAAACAATTTAAACATAGTAGAAT

FIG. 7D (SEQ ID NOs: 27 and 28)

TATCAATAAAATTTCTAATTCCTAAAACCAAATCCAGTACTAAAATCCCCGAATTAATTCGGCGT
TAATTCAGTACATTAAAACGTCCGCAATGTTATTAAGTTGTCTAAGGCTCAATTGTTACCACAATA
AAAACCGTCCCAAACTCTTTCCGTCCTTACAGATTAATCCACACAAACATAGGACTAATGAAAACC
AACCAAACAACCCTATTTGGTAAGCTTCTAGGAGGAGCTTTATACAAAAGCATGATGATTTTCCTAGCCTA
CCCCTCCGGTTACAAACACGCTAATTTCATCCACGAA

IND-10015-7 specific event detection system

IND-10015-7 WT allele

IND-10003-4 specific event detection system

IND-10003-4 WT allele

SEQUENCE LISTING

```
<160> NUMBER OF SEQ ID NOS: 28

<210> SEQ ID NO 1
<211> LENGTH: 7630
<212> TYPE: DNA
<213> ORGANISM: Artificial Sequence
<220> FEATURE:
<223> OTHER INFORMATION: Insert and flanking regions IND-13-4

<400> SEQUENCE: 1
cagttatgtt tggcttatca ctttaatcga tcacaattac accaaatgat tgacgacact      60
aaaatcacca acaaacccc attatattac tctccaaaag aggccttaca aagaggggag     120
agtcccaaca tatatacaag tggctttctt tgtaagcttt ttgcataagc caaatagcta     180
tgagtctatt tggtcaacta tacatgactg tttggtagtg gcttaatgat atagaagttg     240
gcttattcaa aaagcttttg gggtggaccg gccggggggg ggggtggggt gatgtagaaa     300
gccaagtttt tccaaacctg ccctctcga ttaaaaaaca agctccttcc atgtatgaaa      360
aaaccctctc aaacaaaaaa acttctcaag ctatacagac acagattaat ccacacaaac     420
aactttatcc atacatgact tgatggaaaa ccaaccaaca acttcttaga gacggatata     480
tgttcaagaa cattaccagc caaacactga tagtttaaac tgaaggcggg aaacgacaat     540
ctgatccaag ctcaagctgc tctagcattc gccattcagg ctgcgcaact gttgggaagg     600
gcgatcggtg cgggcctctt cgctattacg ccagctggcg aaaggggat gtgctgcaag      660 gcgattaagt tgggtaacgc cagggttttc ccagtcacga cgttgtaaaa cgacggccag     720
tgccaagctt gcatgcctgc aggaattcat tgtactccca gtatcattat agtgaaagtt     780
ttggctctct cgccggtggt tttttacctc tatttaaagg ggttttccac ctaaaaattc     840
tggtatcatt ctcactttac ttgttacttt aatttctcat aatctttggt tgaaattatc     900
acgcttccgc acacgatatc cctacaaatt tattatttgt taaacatttt caaaccgcat     960 aaaatttat gaagtcccgt ctatctttaa tgtagtctaa cattttcata ttgaaatata    1020
taatttactt aattttagcg ttggtagaaa gcataatgat ttattcttat tcttcttcat    1080
ataaatgttt aatatacaat ataaacaaat tctttaccct aagaaggatt tcccattta     1140 tattttaaaa atatatttat caaatatttt tcaaccacgt aaatctcata ataataagtt    1200
gtttcaaaag taataaaatt taactccata atttttttat tcgactgatc ttaaagcaac    1260
acccagtgac acaactagcc atttttttct ttgaataaaa aaatccaatt atcattgtat    1320 ttttttttata caatgaaaat ttcaccaaac aatgatttgt ggtatttctg aagcaagtca    1380
tgttatgcaa aattctataa ttcccatttg acactacgga agtaactgaa gatctgcttt    1440
tacatgcgag acacatcttc taaagtaatt ttaataataag ttactatatt caagatttca    1500
tatatcaaat actcaatatt acttctaaaa aattaattag atataattaa aatattactt    1560
```

```
ttttaatttt aagtttaatt gttgaatttg tgactattga tttattattc tactatgttt    1620
aaattgtttt atagatagtt taaagtaaat ataagtaatg tagtagagtg ttagagtgtt    1680
accctaaacc ataaactata agatttatgg tggactaatt ttcatatatt tcttattgct    1740 tttaccttt  cttggtatgt aagtccgtaa ctgaattac  tgtgggttgc catggcactc    1800
tgtggtcttt tggttcatgc atggatgctt gcgcaagaaa aagacaaaga acaaagaaaa    1860
aagacaaaac agagagacaa aacgcaatca cacaaccaac tcaaattagt cactggctga    1920
tcaagatcgc cgcgtccatg tatgtctaaa tgccatgcaa agcaacacgt gcttaacatg    1980
cactttaaat ggctcaccca tctcaaccca cacacaaaca cattgccttt tcttcatca    2040 tcaccacaac cacctgtata tattcattct cttccgccac ctcaatttct tcacttcaac    2100
acacgtcaac ctgcatatgc gtgtcatccc atgcccaaat ctccatgcat gttccaacca    2160
ccttctctct tatataatac ctataaatac ctctaatatc actcacttct ttcatcatcc    2220
atccatccag agtactacta ctctactact ataatacccc aacccaactc atattcaata    2280
ctactctacc atgaacttcc ttaagtcttt ccctttctac gctttccttt gtttcggtca    2340
atacttcgtt gctgttactc acgctgctga gatcacccgc attcctctct acaaaggtaa    2400
gtctctccgt aaggcgctga aggaacatgg acttctagaa gacttcttgc agaaacaaca    2460
gtatggcatc agcagcaagt actccggctt cggtgaagtt gctagcgtgc cacttaccaa    2520
ctaccttgat agtcaatact ttgggaagat ctacctcgga accccgcctc aagagttcac    2580
cgttctcttt gatactggtt cctctgactt ctgggttccc tctatctact gcaagagcaa    2640
tgcctgcaag aaccaccaaa gattcgatcc gagaaagtcg tccaccttcc agaacttagg    2700 caaaccttg  tctatacact acggtacagg tagcatgcaa ggaatcttag gctatgatac    2760
cgtcactgtc tccaacattg tggacattca acagacagta ggacttagca cccaagaacc    2820
aggtgatgtc ttcacctatg cagaattcga tggcatcctt ggtatggcat acccatcgct    2880
cgcgtcagag tactcgatac ctgtgtttga caacatgatg aaccgacacc tagtagctca    2940
agacttgttc tcggtttaca tggacaggaa tggccaggag agcatgctca cgcttggagc    3000
tattgatcca tcctactaca caggatctct tcactgggtt ccagtcactg tgcagcagta    3060
ctggcaattc actgtggaca gtgtcaccat cagcggtgtg ttgttgcat  gtgaaggtgg    3120 atgtcaagct atcttggata ccggtacgtc caagctggtc ggacctagca gcgacattct    3180
caacattcag caagctattg gagccacaca gaaccagtac ggtgagtttg acatagattg    3240
cgacaacctt agctacatgc ctacagttgt ctttgagatc aacggcaaga tgtacccact    3300
gacccccctc gcctatacca gccaggatca agggttctgc accagtggat tccagagtga    3360
gaaccattcc cagaaatgga tcttgggaga tgtgttcatt cgtgagtact acagcgtctt    3420
tgacagggcc aacaaccctc gttgggctag ctaaagcaatc tgaccatgca tggatcaagc    3480
ttaaataagt atgaactaaa atgcatgtag gtgtaagagc tcatggagag catgaatat     3540 tgtatccgac catgtaacag tataataact gagctccatc tcacttcttc tatgaataaa    3600
caaaggatgt tatgatatat taacactcta tctatgcacc ttattgttct atgataaatt    3660
tcctcttatt attataaatc atctgaatcg tgacggctta tggaatgctt caaatagtac    3720
aaaaacaaat gtgtactata agactttcta acaattcta  actttagcat tgtgaacgag    3780
acataagtgt taagaagaca taacaattat aatggaagaa gtttgtctcc atttatatat    3840
tatatattac ccactatgt  attatattag gatgttaagg agacataaca attataaaga    3900
```

```
gagaagtttg tatccattta tatattatat actacccatt tatatattat acttatccac   3960
ttatttaatg tctttataag gtttgatcca tgatatttct aatattttag ttgatatgta   4020
tatgaaaagg tactatttga actctcttac tctgtataaa ggttggatca tccttaaagt   4080
gggtctattt aattttattg cttcttacag ataaaaaaaa aattatgagt tggtttgata   4140
aaatattgaa ggatttaaaa taataataaa taataaataa catataatat atgtatataa   4200
atttattata atataacatt tatctataaa aaagtaaata ttgtcataaa tctatacaat   4260
cgtttagcct tgctggaacg aatctcaatt atttaaacga gagtaaacat atttgacttt   4320
ttggttattt aacaaattat tatttaacac tatatgaaat tttttttttt tatcagcaaa   4380
gaataaaatt aaattaagaa ggacaatggt gtcccaatcc ttatacaacc aacttccaca   4440
agaaagtcaa gtcagagaca acaaaaaaac aagcaaagga aatttttttaa tttgagttgt   4500
cttgtttgct gcataaattta tgcagtaaaa cactacacat aacccttta gcagtagagc   4560
aatggttgac cgtgtgctta gcttctttta ttttattttt ttatcagcaa agaataaata   4620
aaataaaatg agacacttca gggatgtttc aacccttata caaaacccca aaaacaagtt   4680
tcctagcacc ctaccaacta aggtaccgag ctcagaattc gaatccaaaa attacggata   4740
tgaatatagg catatccgta tccgaattat ccgtttgaca gctagcaacg attgtacaat   4800
tgcttcttta aaaaggaag aaagaaagaa agaaaagaat caacatcagc gttaacaaac   4860
ggccccgtta cggcccaaac ggtcatatag agtaacggcg ttaagcgttg aaagactcct   4920
atcgaaatac gtaaccgcaa acgtgtcata gtcagatccc ctcttccttc accgcctcaa   4980
acacaaaaat aatcttctac agcctatata tacaaccccc ccttctatct ctcctttctc   5040
acaattcatc atctttcttt ctctaccccc aattttaaga aatcctctct tctcctcttc   5100
attttcaagg taaatctctc tctctctctc tctctctgtt attccttgtt ttaattaggt   5160
atgtattatt gctagtttgt taatctgctt atcttatgta tgccttatgt gaatatcttt   5220
atcttgttca tctcatccgt ttagaagcta taaatttgtt gatttgactg tgtatctaca   5280
cgtggttatg tttatatcta atcagatatg aatttcttca tattgttgcg tttgtgtgta   5340
ccaatccgaa atcgttgatt ttttcatttt aatcgtgtag ctaattgtac gtatacatat   5400
ggatctacgt atcaattgtt catctgtttg tgtttgtatg tatacagatc tgaaaacatc   5460
acttctctca tctgattgtg ttgttacata catagatata gatctgttat atcattttt   5520
ttattaattg tgtatatata tatgtgcata gatctggatt acatgattgt gattatttac   5580
atgattttgt tatttacgta tgtatatatg tagatctgga cttttttggag ttgttgactt   5640
gattgtatt tgtgtgtgtat atgtgtgttc tgatcttgat atgttatgta tgtgcagcca   5700
aggctacggg cgatccacca tgtctccgga gaggagacca gttgagatta ggccagctac   5760
agcagctgat atggccgcgg tttgtgatat cgttaaccat tacattgaga cgtctacagt   5820
gaactttagg acagagccac aaacaccaca agagtggatt gatgatctag agaggttgca   5880
agatagatac ccttggttgg ttgctgaggt tgagggtgtt gtggctggta ttgcttacgc   5940
tgggccctgg aaggctagga acgcttacga ttggacagtt gagagtactg tttacgtgtc   6000
acataggcat caaaggttgg gcctaggttc cacattgtac acacatttgc ttaagtctat   6060
ggaggcgcaa ggttttaagt ctgtggttgc tgttataggc cttccaaacg atccatctgt   6120
taggttgcat gaggctttgg gatacacagc ccggggtaca ttgcgcgcag ctggatacaa   6180
gcatggtgga tggcatgatg ttggttttgt gcaaagggat tttgagttgc cagctcctcc   6240
aaggccagtt aggccagtta cccagatctg agtcgaccga atgagttcca agatggtttg   6300
```

```
tgacgaagtt agttggttgt ttttatggaa cttttgtttaa gctagcttgt aatgtggaaa    6360
gaacgtgtgg cttttgtggtt tttaaatgtt ggtgaataaa gatgttttcct ttggattaac   6420 tagtatttt  cctattggtt tcatggtttt agcacacaac atttttaaata tgctgttaga    6480 tgatatgctg cctgctttat tatttactta cccctcacct tcagtttcaa agttgttgca    6540
atgactctgt gtagtttaag atcgagtgaa agtagatttt gtctatattt attaggggta    6600
tttgatatgc taatggtaaa catggtttat gacagcgtac ttttttggtt atggtgttga    6660
cgtttccttt taaacattat agtagcgtcc ttggtctgtg ttcattggtt gaacaaaggc    6720
acactcactt ggagatgccg tctccactga tatttgaaca agaattcgt aatcatgtca     6780 tagctgtttc ctgtgtgaaa ttgttatccg ctcacaattc cacacaacat acgagccgga    6840
agcataaagt gtaaagcctg gggtgcctaa tgagtgagct aactcacatt aattgcgttg    6900
cgctcactgc ccgctttcca gtcgggaaac ctgtcgtgcc agatcgaccc aagtaccgcc    6960
acctaacaat tcgttcaagc cgagatcggc ttcccggcct agagtcgatc gacaagctcg    7020
agtttctcca taataatgtg tgagtagttc ccagataagg gaattagggt tcctataggg    7080
tttcgctcat gtgttgagca tataagaaac ccttagtatg tatttgtatt tgtaaaatac    7140
ttctatcaat aaaatttcta attcctaaaa ccaaaatcca gtactaaaat ccagatcccc    7200
cgaattaatt cggcgttaat tcagtacatt aaaaacgtcc gcaatgtgtt attaagttgt    7260
ctaaggctag gaacgcttac gattggccct tttgccagca ttccgatcaa gctcactatc    7320
agtcaacggt tcgaacatga aacaatgcaa agtaatccca atcgatccac cttgtttacg    7380
ctgcacagag aaacccaaat taaactatga acaatatttt tcttcaccaa cgtgcaaaag    7440
tacatcaatc caacaatgcc aatagatcat ggcttaaaaa tagagttaaa attagttgat    7500
tgcctgaaac ttgtcacgat atagcttggc tgccatgcca tgggccagta acatgttgtg    7560
cataacaatg agaggctcaa cgtctgaatt tccagcaaca cagttgccaa agggctctga    7620
acaacgagaa                                                            7630
```

<210> SEQ ID NO 2
<211> LENGTH: 8324
<212> TYPE: DNA
<213> ORGANISM: Artificial Sequence
<220> FEATURE:
<223> OTHER INFORMATION: Insert and flanking regions IND-115-7

<400> SEQUENCE: 2

```
aaatggctca tttaggagct gtaacagcta actgggtaag agtgtgatct gggtaagtac      60
caactgaaat tggtttttac tgctaaaaga ttaccattat aaccctctga aaaacccttta   120 tcacaaaaag atggtagccc ttgaaagtgc gtaaactaga gacatgttgt tagcagctta    180
atgagcttaa tctggctcgc aacttattcg gtcagcaatg caatgtatag aaagtaagtc    240
ccgtttgtta gcaacttaat gagcttaata ggactgagaa cttattcggt cagctataaa    300
tgactgtgtg gtagttggct tgatgatatt gaaagtgact tattcgttaa gatttacggg    360
ggagctttat gcagaaatcc acagagtgcc atggcaaccc acagtaattc cagttacgga    420
cttacatacc aagaaaaggt aaaagcaata agaaatatat gaaaattagt ccaccataaa    480
tcttatagtt tatggtttag ggtaacactc taacactcta ctacattact tatatttact    540
ttaaactatc tataaaacaa tttaaacata gtagaataat aaatcaatag tcacaaattc    600
aacaattaaa cttaaaatta aaaagtaat atttttaatta tatctaatta attttttaga    660
```

```
agtaatattg agtatttgat atatgaaatc ttgaatatag taactattat taaaattact    720
ttagaagatg tgtctcgcat gtaaaagcag atcttcagtt acttccgtag tgtcaaatgg    780
gaattataga attttgcata acatgacttg cttcagaaat accacaaatc attgtttggt    840
gaaattttca ttgtataaaa aaaatacaat gataattgga ttttttttatt caaagaaaaa    900
aatggctagt tgtgtcactg ggtgttgctt taagatcagt cgaataaaaa aattatggag    960
ttaaatttta ttacttttga aacaacttat tattatgaga tttacgtggt tgaaaaatat   1020
ttgataaata tattttaaa atataaaatg ggaaatcctt cttaaggtaa agaatttgtt   1080
tatattgtat attaaacatt tatatgaaga agaataagaa taaatcatta tgctttctac   1140
caacgctaaa attaagtaaa ttatatattt caatatgaaa atgttagact acattaaaga   1200
tagacgggac ttcataaaat tttatgcggt ttgaaaatgt ttaacaaata ataaatttgt   1260
agggatatcg tgtgcggaag cgtgataatt tcaaccaaag attatgagaa attaaagtaa   1320
caagtaaagt gagaatgata ccagaatttt taggtggaaa accccttttaa atagaggtaa   1380
aaaaccaccg gcgagagagc caaaactttc actataatga tactgggagt acaatgaatt   1440
cctgcaggca tgcaagcttg gcactggccg tcgttttaca acgtcgtgac tgggaaaacc   1500
ctggcgttac ccaacttaat cgccttgcag cacatccccc tttcgccagc tggcgtaata   1560
gcgaagaggc ccgcaccgat cgcccttccc aacagttgcg cagcctgaat ggcgaatgct   1620
agagcagctt gagcttggat cagattgtcg tttcccgcct tcagtttaaa ctatcagtgt   1680
ttgaacactg atagtttaaa ctgaaggcgg gaaacgacaa tctgatccaa gctcaagctg   1740
ctctagcatt cgggaattca cgttttttctt tgaataaaaa aatccaatta tcattgtatt   1800
ttttttatac aatgaaaatt tcaccaaaca atgatttgtg gtatttctga agcaagtcat   1860
gttatgcaaa attctataat tcccatttga cactacggaa gtaactgaag atctgctttt   1920
acatgcgaga cacatcttct aaagtaattt taataatagt tactatattc aagatttcat   1980
atatcaaata ctcaatatta cttctaaaaa attaattaga taaattaaaa atattacttt   2040
tttaattta agtttaattg ttgaatttgt gactattgat ttattattct actatgttta   2100
aattgtttta tagatagttt aaagtaaata taagtaatgt agtagagtgt tagagtgtta   2160
ccctaaaacca taaactataa gatttatggt ggactaattt tcatatattt cttattgctt   2220
ttacctttc ttggtatgta agtccgtaac tggaattact gtgggttgcc atggcactct   2280
gtggtctttt ggttcatgca tggatgcttg cgcaagaaaa agacaaagaa caaagaaaaa   2340
agacaaaaca gagagacaaa acgcaatcac acaaccaact caaattagtc actggctgat   2400
caagatcgcc gcgtccatgt atgtctaaat gccatgcaaa gcaacacgtg cttaacatgc   2460
actttaaatg gctcacccat ctcaacccac acacaaacac attgcctttt tcttcatcat   2520
caccacaacc acctgtatat attcattctc ttccgccacc tcaatttctt cacttcaaca   2580
cacgtcaacc tgcatatgcg tgtcatccca tgcccaaatc tccatgcatg ttccaaccac   2640
cttctctctt atataatacc tataaatacc tctaatatca ctcacttctt tcatcatcca   2700
tccatccaga gtactactac tctactacta taatacccca acccaactca tattcaatac   2760
tactctacta tgaacttcct taagtctttc cctttctacg ctttcctttg tttcggtcaa   2820
tacttcgttg ctgttactca cgctgctgag atcacccgca ttcctctcta caaaggtaag   2880
tctctccgta aggcgctgaa ggaacatgga cttctagaag acttcttgca gaaacaacag   2940
tatggcatca gcagcaagta ctccggcttc ggtgaagttg ctagcgtgcc acttaccaac   3000
taccttgata gtcaatactt tgggaagatc tacctcggaa ccccgcctca agagttcacc   3060
```

```
gttctctttg atactggttc ctctgacttc tgggttccct ctatctactg caagagcaat    3120
gcctgcaaga accaccaaag attcgatccg agaaagtcgt ccaccttcca gaacttaggc    3180
aaacccttgt ctatacacta cggtacaggt agcatgcaag gaatcttagg ctatgatacc    3240
gtcactgtct ccaacattgt ggacattcaa cagacagtag gacttagcac ccaagaacca    3300
ggtgatgtct tcacctatgc agaattcgat ggcatccttg gtatggcata cccatcgctc    3360
gcgtcagagt actcgatacc tgtgtttgac aacatgatga accgacacct agtagctcaa    3420
gacttgttct cggtttacat ggacaggaat ggccaggaga gcatgctcac gcttggagct    3480
attgatccat cctactacac aggatctctt cactgggttc cagtcactgt gcagcagtac    3540
tggcaattca ctgtggacag tgtcaccatc agcggtgtgg ttgttgcatg tgaaggtgga    3600
tgtcaagcta tcttggatac cggtacgtcc aagctggtcg gacctagcag cgacattctc    3660
aacattcagc aagctattgg agccacacag aaccagtacg gtgagtttga catagattgc    3720
gacaacctta gctacatgcc tacagttgtc tttgagatca acggcaagat gtacccactg    3780
accccctccg cctataccag ccaggatcaa gggttctgca ccagtggatt ccagagtgag    3840
aaccattccc agaaatggat cttgggagat gtgttcattc gtgagtacta cagcgtcttt    3900
gacagggcca caacctcgt tgggctagct aaagcaatct gaccatgcat ggatcaagct    3960
taaataagta tgaactaaaa tgcatgtagg tgtaagagct catggagagc atggaatatt    4020
gtatccgacc atgtaacagt ataataactg agctccatct cacttcttct atgaataaac    4080
aaaggatgtt atgatatatt aacactctat ctatgcacct tattgttcta tgataaattt    4140
cctcttatta ttataaatca tctgaatcgt gacggcttat ggaatgcttc aaatagtaca    4200
aaaacaaatg tgtactataa gactttctaa acaattctaa ctttagcatt gtgaacgaga    4260
cataagtgtt aagaagacat aacaattata atggaagaag tttgtctcca tttatatatt    4320
atatattacc cacttatgta ttatattagg atgttaagga gacataacaa tttataaagag    4380 agaagtttgt atccatttat atattatata ctacccattt atatattata cttatccact    4440
tatttaatgt ctttataagg tttgatccat gatatttcta atattttagt tgatatgtat    4500
atgaaaaggt actatttgaa ctctcttact ctgtataaag gttggatcat ccttaaagtg    4560
ggtctattta atttattgc ttcttacaga taaaaaaaaa attatgagtt ggtttgataa    4620
aatattgaag gatttaaaat aataataaat aataaataac atataatata tgtatatataa    4680 tttattataa tataacattt atctataaaa aagtaaatat tgtcataaat ctatacaatc    4740
gtttagcctt gctggaacga atctcaatta tttaaacgag agtaaacata tttgactttt    4800 tggttatta acaaattatt atttaacact atatgaaatt ttttttttt atcagcaaag    4860 aataaaatta aattaagaag gacaatggtg tcccaatcct tatacaacca acttccacaa    4920
gaaagtcaag tcagagacaa caaaaaaaca agcaaaggaa attttttaat ttgagttgtc    4980
ttgtttgctg cataatttat gcagtaaaac actacacata acccttttag cagtagagca    5040
atggttgacc gtgtgcttag cttctttat ttatttttt tatcagcaaa gaataaataa    5100
aataaaatga gacacttcag ggatgtttca accccttatac aaaacccaa aaacaagttt    5160 cctagcaccc taccaactaa ggtaccgagc tcagaattcg aatccaaaaa ttacggatat    5220
gaatataggc atatccgtat ccgaattatc cgtttgacag ctagcaacga ttgtacaatt    5280
gcttctttaa aaaggaaga aagaaagaaa gaaaagaatc aacatcagcg ttaacaaacg    5340
gccccgttac ggcccaaacg gtcatataga gtaacggcgt taagcgttga aagactccta    5400
```

```
tcgaaatacg taaccgcaaa cgtgtcatag tcagatcccc tcttccttca ccgcctcaaa   5460
cacaaaaata atcttctaca gcctatatat acaaccccc  cttctatctc tcctttctca   5520
caattcatca tctttctttc tctaccccca attttaagaa atcctctctt ctcctcttca   5580
ttttcaaggt aaatctctct ctctctctct ctctctgtta ttccttgttt taattaggta   5640
tgtattattg ctagtttgtt aatctgctta tcttatgtat gccttatgtg aatatcttta   5700
tcttgttcat ctcatccgtt tagaagctat aaatttgttg atttgactgt gtatctacac   5760
gtggttatgt ttatatctaa tcagatatga atttcttcat attgttgcgt ttgtgtgtac   5820
caatccgaaa tcgttgattt ttttcattta atcgtgtagc taattgtacg tatacatatg   5880
gatctacgta tcaattgttc atctgtttgt gtttgtatgt atacagatct gaaaacatca   5940
cttctctcat ctgattgtgt tgttacatac atagatatag atctgttata tcatttttt    6000 tattaattgt gtatatatat atgtgcatag atctggatta catgattgtg attatttaca   6060
tgattttgtt atttacgtat gtatatatgt agatctggac ttttggagt tgttgacttg    6120 attgtatttg tgtgtgtata tgtgtgttct gatcttgata tgttatgtat gtgcagccaa   6180
ggctacgggc gatccaccat gtctccggag aggagaccag ttgagattag ccagctaca    6240 gcagctgata tggccgcgt  ttgtgatatc gttaaccatt acattgagac gtctacagtg   6300
aactttagga cagagccaca aacaccacaa gagtggattg atgatctaga gaggttgcaa   6360
gatagatacc cttggttggt tgctgaggtt gagggtgttg tggctggtat tgcttacgct   6420
gggccctgga aggctaggaa cgcttacgat tggacagttg agagtactgt ttacgtgtca   6480
cataggcatc aaaggtgggg cctaggttcc acattgtaca cacatttgct taagtctatg   6540
gaggcgcaag gttttaagtc tgtggttgct gttataggcc ttccaaacga tccatctgtt   6600
aggttgcatg aggctttggg atacacagcc cggggtacat gcgcgcagc  tggatacaag   6660 catggtggat ggcatgatgt tggtttttgg caaagggatt ttgagttgcc agctcctcca   6720
aggccagtta ggccagttac ccagatctga gtcgaccgaa tgagttccaa gatggtttgt   6780
gacgaagtta gttggttgtt tttatggaac tttgtttaag ctagcttgta atgtggaaag   6840
aacgtgtggc tttgtggttt ttaaatgttg gtgaataaag atgtttcctt tggattaact   6900 agtattttc ctattggttt catggtttta gcacacaaca ttttaaatat gctgttagat    6960
gatatgctgc ctgctttatt atttacttac ccctcacctt cagtttcaaa gttgttgcaa   7020
tgactctgtg tagtttaaga tcgagtgaaa gtagattttg tctatattta ttaggggtat   7080
ttgatatgct aatggtaaac atggtttatg acagcgtact ttttttggtta tggtgttgac   7140 gtttcctttt aaacattata gtagcgtcct tggtctgtgt tcattggttg aacaaaggca   7200
cactcacttg gagatgccgt ctccactgat atttgaacaa agaattcgta atcatgtcat   7260
agctgtttcc tgtgtgaaat tgttatccgc tcacaattcc acacaacata cgagccggaa   7320
gcataaagtg taaagcctgg ggtgcctaat gagtgagcta actcacatta attgcgttgc   7380
gctcactgcc cgctttccag tcgggaaacc tgtcgtgcca gatcgaccca agtaccgcca   7440
cctaacaatt cgttcaagcc gagatcggct tcccggccta gagtcgatcg acaagctcga   7500
gtttctccat aataatgtgt gagtagtcc  cagataaggg aattagggtt cctatagggt    7560
ttcgctcatg tgttgagcat ataagaaacc cttagtatgt atttgtattt gtaaaatact   7620
tctatcaata aaatttctaa ttcctaaaac caaaatccag tactaaaatc cagatccccc   7680
gaattaattc ggcgttaatt cagtacatta aaaacgtccg caatgtgtta ttaagttgtc   7740
taagcgtcaa tttgtttaca ccacaataaa aaaccgtccc aaacaaaatc ttttccgtcc   7800
```

```
ttacagatta atccacacaa acataggact taatgaaaac caaccaaaca acccctattt      7860
ggtaagcttc tagggaggag ctttatacaa aaagccatga ttttcctag cctaccctc       7920
```
*(line 7920: "ttttcctag" as shown)*

```
ccggttacaa acacgctaat ttcatccacg aaaaaactct ccaaaaaaaa atctttcgca      7980
gtgtatatag acagattaat caacacagac aactttatat gtgcagaact aagtggaaaa     8040
tcagacgaac aaatgcacaa tatatattta aagaccatat atttacctca atggcgtcga     8100
ctgtgagagg caggacgatg actttctcag agaacttctg tttctcagct gcatcacgag     8160
caagccgacg acggtaagag aaattgttga acaaagctct gagctccttc agctttccct     8220
tagcaacagc caattcacga agtgcacgaa gagcctgaga tctcctgatc agataagccc     8280
taaaagtcat ctggatcacc atggctgcat cctgaggtga taac                      8324
```

```
<210> SEQ ID NO 3
<211> LENGTH: 378
<212> TYPE: DNA
<213> ORGANISM: Artificial Sequence
<220> FEATURE:
<223> OTHER INFORMATION: Right junction Sequence IND-13-4

<400> SEQUENCE: 3
aaatggctca tttaggagct gtaacagcta actgggtaag agtgtgatct gggtaagtac       60
caactgaaat tggttttac tgctaaaaga ttaccattat aaccctctga aaaccctta       120
```
*(line 120: as shown)*

```
tcacaaaaag atggtagccc ttgaaagtgc gtaaactaga gacatgttgt tagcagctta     180
atgagcttaa tctggctcgc aacttattcg gtcagcaatg caatgtatag aaagtaagtc     240
ccgtttgtta gcaacttaat gagcttaata ggactgagaa cttattcggt cagctataaa     300
tgactgtgtg gtagttggct tgatgatatt gaaagtgact tattcgttaa gatttacggg     360
ggagctttat gcagaaat                                                   378
```

```
<210> SEQ ID NO 4
<211> LENGTH: 580
<212> TYPE: DNA
<213> ORGANISM: Artificial Sequence
<220> FEATURE:
<223> OTHER INFORMATION: Left junction Sequence IND-13-4

<400> SEQUENCE: 4
cgtcaatttg tttacaccac aataaaaaac cgtcccaaac aaaatctttt ccgtccttac       60
agattaatcc acacaaacat aggacttaat gaaaaccaac caaacaaccc ctatttggta     120
agcttctagg gaggagcttt atacaaaaag ccatgatttt tcctagccta cccctcccgg     180
ttacaaacac gctaatttca tccacgaaaa aactctccaa aaaaaatct ttcgcagtgt      240
```
*(line 240: as shown)*

```
atatagacag attaatcaac acagacaact ttatatgtgc agaactaagt ggaaaatcag     300
acgaacaaat gcacaatata tatttaaaga ccatatattt acctcaatgg cgtcgactgt     360
gagaggcagg acgatgactt tctcagagaa cttctgtttc tcagctgcat cacgagcaag     420
ccgacgacgg taagagaaat tgttgaacaa agctctgagc tccttcagct ttcccttagc     480
aacagccaat tcacgaagtg cacgaagagc ctgagatctc tgatcagat aagccctaaa     540
```
*(line 540: as shown)*

```
agtcatctgg atcaccatgg ctgcatcctg aggtgataac                           580
```

```
<210> SEQ ID NO 5
<211> LENGTH: 500
<212> TYPE: DNA
<213> ORGANISM: Artificial Sequence
<220> FEATURE:
```

<223> OTHER INFORMATION: Right junction Sequence IND-115-7

<400> SEQUENCE: 5

```
cagttatgtt tggcttatca ctttaatcga tcacaattac accaaatgat tgacgacact    60
aaaatcacca acaaaccccc attatattac tctccaaaag aggccttaca aagaggggag   120
agtcccaaca tatatacaag tggctttctt tgtaagcttt ttgcataagc caaatagcta   180
tgagtctatt tggtcaacta tacatgactg tttggtagtg gcttaatgat atagaagttg   240
gcttattcaa aaagcttttg gggtggaccg gccggggggg ggggtggggt gatgtagaaa   300
gccaagtttt tccaaacctg cccctctcga ttaaaaaaca agctccttcc atgtatgaaa   360
aaaccctctc aaacaaaaaa acttctcaag ctatacagac acagattaat ccacacaaac   420
aactttatcc atacatgact tgatggaaaa ccaaccaaca acttcttaga gacggatata   480
tgttcaagaa cattaccagc                                              500
```

<210> SEQ ID NO 6
<211> LENGTH: 365
<212> TYPE: DNA
<213> ORGANISM: Artificial Sequence
<220> FEATURE:
<223> OTHER INFORMATION: Left junction Sequence IND-115-7

<400> SEQUENCE: 6

```
gctaggaacg cttacgattg gcccttttgc cagcattccg atcaagctca ctatcagtca    60
acggttcgaa catgaaacaa tgcaaagtaa tcccaatcga tccaccttgt ttacgctgca   120
cagagaaacc caaattaaac tatgaacaat attttcttc accaacgtgc aaaagtacat   180
caatccaaca atgccaatag atcatggctt aaaaatagag ttaaaattag ttgattgcct   240
gaaacttgtc acgatatagc ttggctgcca tgccatgggc cagtaacatg ttgtgcataa   300
caatgagagg ctcaacgtct gaatttccag caacacagtt gccaagggc tctgaacaac   360
gagaa                                                              365
```

<210> SEQ ID NO 7
<211> LENGTH: 6765
<212> TYPE: DNA
<213> ORGANISM: Artificial Sequence
<220> FEATURE:
<223> OTHER INFORMATION: Insert Sequence

<400> SEQUENCE: 7

```
caaacactga tagtttaaac tgaaggcggg aaacgacaat ctgatccaag ctcaagctgc    60
tctagcattc gccattcagg ctgcgcaact gttgggaagg gcgatcggtg cgggcctctt   120
cgctattacg ccagctggcg aaagggggat gtgctgcaag gcgattaagt tgggtaacgc   180
cagggttttc ccagtcacga cgttgtaaaa cgacggccag tgccaagctt gcatgcctgc   240
aggaattcat tgtactccca gtatcattat agtgaaagtt ttggctctct cgccggtggt   300
tttttacctc tatttaaagg ggttttccac ctaaaaattc tggtatcatt ctcactttac   360
ttgttacttt aatttctcat aatctttggt tgaaattatc acgcttccgc acacgatatc   420
cctacaaatt tattatttgt taaacatttt caaaccgcat aaaattttat gaagtcccgt   480
ctatctttaa tgtagtctaa catttcata ttgaaatata aatttactt aattttagcg   540
ttggtagaaa gcataatgat ttattcttat tcttcttcat ataaatgttt aatatacaat   600
ataaacaaat tctttacctt aagaaggatt tcccatttta tattttaaaa atatatttat   660
caaatatttt tcaaccacgt aaatctcata ataataagtt gtttcaaaag taataaaatt   720
```

```
taactccata attttttat tcgactgatc ttaaagcaac acccagtgac acaactagcc      780 atttttct ttgaataaaa aaatccaatt atcattgtat ttttttata caatgaaaat        840 ttcaccaaac aatgatttgt ggtatttctg aagcaagtca tgttatgcaa aattctataa    900
ttcccatttg acactacgga agtaactgaa gatctgcttt tacatgcgag acacatcttc    960
taaagtaatt ttaataatag ttactatatt caagatttca tatatcaaat actcaatatt   1020
acttctaaaa aattaattag atataattaa aatattactt ttttaatttt aagtttaatt   1080
gttgaatttg tgactattga tttattattc tactatgttt aaattgtttt atagatagtt   1140
taaagtaaat ataagtaatg tagtagagtg ttagagtgtt accctaaacc ataaactata   1200
agatttatgg tggactaatt ttcatatatt tcttattgct tttaccttt cttggtatgt    1260 aagtccgtaa ctggaattac tgtgggttgc catggcactc tgtggtcttt tggttcatgc   1320
atggatgctt gcgcaagaaa aagacaaaga acaagaaaa aagacaaaac agagagacaa    1380
aacgcaatca cacaaccaac tcaaattagt cactggctga tcaagatcgc cgcgtccatg   1440
tatgtctaaa tgccatgcaa agcaacacgt gcttaacatg cactttaaat ggctcaccca   1500
tctcaaccca cacacaaaca cattgccttt ttcttcatca tcaccacaac cacctgtata   1560
tattcattct cttccgccac ctcaatttct tcacttcaac acacgtcaac ctgcatatgc   1620
gtgtcatccc atgcccaaat ctccatgcat gttccaacca ccttctctct tatataatac   1680
ctataaatac ctctaatatc actcacttct ttcatcatcc atccatccag agtactacta   1740
ctctactact ataataccc aacccaactc atattcaata ctactctacc atgaacttcc    1800
ttaagtcttt cccttttctac gctttccttt gtttcggtca atacttcgtt gctgttactc   1860
acgctgctga gatcacccgc attcctctct acaaaggtaa gtctctccgt aaggcgctga   1920
aggaacatgg acttctagaa gacttcttgc agaaacaaca gtatggcatc agcagcaagt   1980
actccggctt cggtgaagtt gctagcgtgc cacttaccaa ctaccttgat agtcaatact   2040
ttgggaagat ctacctcgga accccgcctc aagagttcac cgttctcttt gatactggtt   2100
cctctgactt ctgggttccc tctatctact gcaagagcaa tgcctgcaag aaccaccaaa   2160
gattcgatcc gagaaagtcg tccaccttcc agaacttagg caaacccttg tctatacact   2220
acggtacagg tagcatgcaa ggaatcttag gctatgatac cgtcactgtc tccaacattg   2280
tggacattca acagacagta ggacttagca cccaagaacc aggtgatgtc ttcacctatg   2340
cagaattcga tggcatcctt ggtatggcat acccatcgct cgcgtcagag tactcgatac   2400
ctgtgtttga caacatgatg aaccgacacc tagtagctca agacttgttc tcggtttaca   2460
tggacaggaa tggccaggag agcatgctca cgcttggagc tattgatcca tcctactaca   2520
caggatctct tcactgggtt ccagtcactg tgcagcagta ctggcaattc actgtggaca   2580
gtgtcaccat cagcggtgtg gttgttgcat gtgaaggtgg atgtcaagct atcttggata   2640
ccggtacgtc caagctggtc ggacctagca gcgacattct caacattcag caagctattg   2700
gagccacaca gaaccagtac ggtgagtttg acatagattg cgacaacctt agctacatgc   2760
ctacagttgt ctttgagatc aacggcaaga tgtacccact gacccctcc gcctatacca    2820 gccaggatca agggttctgc accagtggat tccagagtga gaaccattcc cagaaatgga   2880
tcttgggaga tgtgttcatt cgtgagtact acagcgtctt tgacagggcc aacaacctcg   2940
ttgggctagc taaagcaatc tgaccatgca tggatcaagc ttaaataagt atgaactaaa   3000
atgcatgtag gtgtaagagc tcatggagag catggaatat tgtatccgac catgtaacag   3060
```

```
tataataact gagctccatc tcacttcttc tatgaataaa caaaggatgt tatgatatat    3120
taacactcta tctatgcacc ttattgttct atgataaatt tcctcttatt attataaatc    3180
atctgaatcg tgacggctta tggaatgctt caaatagtac aaaaacaaat gtgtactata    3240
agactttcta aacaattcta actttagcat tgtgaacgag acataagtgt taagaagaca    3300
taacaattat aatggaagaa gtttgtctcc atttatatat tatatattac ccacttatgt    3360
attatattag gatgttaagg agacataaca attataaaga gagaagtttg tatccattta    3420
tatattatat actacccatt tatatattat acttatccac ttatttaatg tctttataag    3480
gtttgatcca tgatatttct aatattttag ttgatatgta tatgaaaagg tactatttga    3540
actctcttac tctgtataaa ggttggatca tccttaaagt gggtctattt aattttattg    3600
cttcttacag ataaaaaaaa aattatgagt tggtttgata aaatattgaa ggatttaaaa    3660
taataataaa taataaataa catataatat atgtatataa atttattata atataacatt    3720
tatctataaa aaagtaaata ttgtcataaa tctatacaat cgtttagcct tgctggaacg    3780
aatctcaatt atttaaacga gagtaaacat atttgacttt ttggttattt aacaaattat    3840
tatttaacac tatatgaaat ttttttttttt tatcagcaaa gaataaaatt aaattaagaa    3900
ggacaatggt gtcccaatcc ttatacaacc aacttccaca agaaagtcaa gtcagagaca    3960
acaaaaaaac aagcaaagga aattttttaa tttgagttgt cttgtttgct gcataattta    4020
tgcagtaaaa cactacacat aacccttttta gcagtagagc aatggttgac cgtgtgctta    4080
gcttctttta ttttatttt ttatcagcaa agaataaata aaataaaatg agacacttca    4140
gggatgtttc aaccctttata caaaccccca aaaacaagtt tcctagcacc ctaccaacta    4200
aggtaccgag ctcagaattc gaatccaaaa attacggata tgaatatagg catatccgta    4260
tccgaattat ccgtttgaca gctagcaacg attgtacaat tgcttcttta aaaaggaag    4320 aaagaaagaa agaaaagaat caacatcagc gttaacaaac ggccccgtta cggcccaaac    4380
ggtcatatag agtaacggcg ttaagcgttg aaagactcct atcgaaatac gtaaccgcaa    4440
acgtgtcata gtcagatccc ctcttccttc accgcctcaa acacaaaaat aatcttctac    4500
agcctatata tacaacccccc ccttctatct ctcctttctc acaattcatc atctttcttt    4560
ctctaccccc aattttaaga aatcctctct tctcctcttc attttcaagg taaatctctc    4620
tctctctctc tctctctgtt attccttgtt ttaattaggt atgtattatt gctagtttgt    4680
taatctgctt atcttatgta tgccttatgt gaatatcttt atcttgttca tctcatccgt    4740
ttagaagcta taaatttgtt gatttgactg tgtatctaca cgtggttatg tttatatcta    4800
atcagatatg aatttcttca tattgttgcg tttgtgtgta ccaatccgaa atcgttgatt    4860
tttttcattt aatcgtgtag ctaattgtac gtatacatat ggatctacgt atcaattgtt    4920
catctgtttg tgtttgtatg tatacagatc tgaaaacatc acttctctca tctgattgtg    4980
ttgttacata catagatata gatctgttat atcattttttt ttattaattg tgtatatata    5040
tatgtgcata gatctggatt acatgattgt gattatttac atgattttgt tatttacgta    5100
tgtatatatg tagatctgga cttttttggag ttgttgactt gattgtattt gtgtgtgtat    5160
atgtgtgttc tgatcttgat atgttatgta tgtgcagcca aggctacggg cgatccacca    5220
tgtctccgga gaggagacca gttgagatta ggccagctac agcagctgat atggccgcgg    5280
tttgtgatat cgttaaccat tacattgaga cgtctacagt gaactttagg acagagccac    5340
aaacaccaca agagtggatt gatgatctag agaggttgca agatagatac ccttggttgg    5400
ttgctgaggt tgagggtgtt gtggctggta ttgcttacgc tgggccctgg aaggctagga    5460
```

```
acgcttacga ttggacagtt gagagtactg tttacgtgtc ataggcat caaaggttgg   5520 gcctaggttc acattgtac acacattgc ttaagtctat ggaggcgcaa ggttttaagt   5580
ctgtggttgc tgttataggc cttccaaacg atccatctgt taggttgcat gaggcttgg    5640 gatacacagc ccggggtaca ttgcgcgcag ctggatacaa gcatggtgga tgcatgatg    5700 ttggtttttg gcaaagggat tttgagttgc cagctcctcc aaggccagtt aggccagtta   5760
cccagatctg agtcgaccga atgagttcca agatggtttg tgacgaagtt agttggttgt   5820
ttttatggaa ctttgtttaa gctagcttgt aatgtggaaa gaacgtgtgg ctttgtggtt   5880
tttaaatgtt ggtgaataaa gatgtttcct ttggattaac tagtatttt cctattggtt    5940 tcatggtttt agcacacaac attttaaata tgctgttaga tgatatgctg cctgctttat   6000
tatttactta cccctcacct tcagtttcaa agttgttgca atgactctgt gtagtttaag   6060
atcgagtgaa agtagatttt gtctatattt attagggta tttgatatgc taatggtaaa    6120
catggtttat gacagcgtac ttttttggtt atggtgttga cgtttccttt taaacattat   6180
agtagcgtcc ttggtctgtg ttcattggtt gaacaaaggc acactcactt ggagatgccg   6240
tctccactga tatttgaaca agaattcgt atcatgtca tagctgtttc ctgtgtgaaa     6300
ttgttatccg ctcacaattc cacacaacat acgagccgga agcataaagt gtaaagcctg   6360
gggtgcctaa tgagtgagct aactcacatt aattgcgttg cgctcactgc ccgctttcca   6420
gtcgggaaac ctgtcgtgcc agatcgaccc aagtaccgcc acctaacaat tcgttcaagc   6480
cgagatcggc ttcccggcct agagtcgatc gacaagctcg agtttctcca taataatgtg   6540
tgagtagttc ccagataagg gaattagggt tcctataggg tttcgctcat gtgttgagca   6600
tataagaaac ccttagtatg tatttgtatt tgtaaaatac ttctatcaat aaaatttcta   6660
attcctaaaa ccaaaatcca gtactaaaat ccagatcccc gaattaatt cggcgttaat    6720 tcagtacatt aaaaacgtcc gcaatgtgtt attaagttgt ctaag                   6765

<210> SEQ ID NO 8
<211> LENGTH: 19
<212> TYPE: DNA
<213> ORGANISM: Artificial Sequence
<220> FEATURE:
<223> OTHER INFORMATION: Primer 15

<400> SEQUENCE: 8
cacagtcgac gccattgag                                                 19

<210> SEQ ID NO 9
<211> LENGTH: 22
<212> TYPE: DNA
<213> ORGANISM: Artificial Sequence
<220> FEATURE:
<223> OTHER INFORMATION: Primer 16

<400> SEQUENCE: 9
tcctaaaacc aaaatccagt ac                                             22

<210> SEQ ID NO 10
<211> LENGTH: 20
<212> TYPE: DNA
<213> ORGANISM: Artificial Sequence
<220> FEATURE:
<223> OTHER INFORMATION: Primer 707

<400> SEQUENCE: 10
```
gcaacaccca gtgacacaac                                               20

<210> SEQ ID NO 11
<211> LENGTH: 21
<212> TYPE: DNA
<213> ORGANISM: Artificial Sequence
<220> FEATURE:
<223> OTHER INFORMATION: Primer 1170

<400> SEQUENCE: 11
aaatggctca tttaggagct g                                             21

<210> SEQ ID NO 12
<211> LENGTH: 21
<212> TYPE: DNA
<213> ORGANISM: Artificial Sequence
<220> FEATURE:
<223> OTHER INFORMATION: Primer 656

<400> SEQUENCE: 12
tgaaattgag gttggctttc a                                             21

<210> SEQ ID NO 13
<211> LENGTH: 22
<212> TYPE: DNA
<213> ORGANISM: Artificial Sequence
<220> FEATURE:
<223> OTHER INFORMATION: Primer 13

<400> SEQUENCE: 13
tatgttcaag aacattacca gc                                            22

<210> SEQ ID NO 14
<211> LENGTH: 20
<212> TYPE: DNA
<213> ORGANISM: Artificial Sequence
<220> FEATURE:
<223> OTHER INFORMATION: Primer 1090

<400> SEQUENCE: 14
cgaatgctag agcagcttga                                               20

<210> SEQ ID NO 15
<211> LENGTH: 20
<212> TYPE: DNA
<213> ORGANISM: Artificial Sequence
<220> FEATURE:
<223> OTHER INFORMATION: Probe 1091

<400> SEQUENCE: 15
tgaaggcggg aaacgacaat                                               20

<210> SEQ ID NO 16
<211> LENGTH: 20
<212> TYPE: DNA
<213> ORGANISM: Artificial Sequence
<220> FEATURE:
<223> OTHER INFORMATION: Primer 716

<400> SEQUENCE: 16
cttttgcacg ttggtgaaga                                               20

<210> SEQ ID NO 17
<211> LENGTH: 24
<212> TYPE: DNA
<213> ORGANISM: Artificial Sequence

```
<220> FEATURE:
<223> OTHER INFORMATION: Primer 1099

<400> SEQUENCE: 17
ggagaggaga ccagttgaga ttag                                              24

<210> SEQ ID NO 18
<211> LENGTH: 21
<212> TYPE: DNA
<213> ORGANISM: Artificial Sequence
<220> FEATURE:
<223> OTHER INFORMATION: Primer 1546

<400> SEQUENCE: 18
gtgtggtagt tggcttgatg a                                                 21

<210> SEQ ID NO 19
<211> LENGTH: 20
<212> TYPE: DNA
<213> ORGANISM: Artificial Sequence
<220> FEATURE:
<223> OTHER INFORMATION: Primer 1547

<400> SEQUENCE: 19
ctggaattac tgtgggttgc                                                   20

<210> SEQ ID NO 20
<211> LENGTH: 24
<212> TYPE: DNA
<213> ORGANISM: Artificial Sequence
<220> FEATURE:
<223> OTHER INFORMATION: Probe 1548

<400> SEQUENCE: 20
tgcagaaatc cacagagtgc catg                                              24

<210> SEQ ID NO 21
<211> LENGTH: 170
<212> TYPE: DNA
<213> ORGANISM: Artificial Sequence
<220> FEATURE:
<223> OTHER INFORMATION: Left flanking regions IND-115-7

<400> SEQUENCE: 21
ttaaaaaaca agctccttcc atgtatgaaa aaaccctctc aaacaaaaaa acttctcaag        60
ctatacagac acagattaat ccacacaaac aactttatcc atacatgact tgatggaaaa      120
ccaaccaaca acttcttaga gacggatata tgttcaagaa cattaccagc                 170

<210> SEQ ID NO 22
<211> LENGTH: 226
<212> TYPE: DNA
<213> ORGANISM: Artificial Sequence
<220> FEATURE:
<223> OTHER INFORMATION: Left border Insert IND-115-7

<400> SEQUENCE: 22
caaacactga tagtttaaac tgaaggcggg aaacgacaat ctgatccaag ctcaagctgc        60
tctagcattc gccattcagg ctgcgcaact gttgggaagg gcgatcggtg cgggcctctt      120
cgctattacg ccagctggcg aaaggggat gtgctgcaag gcgattaagt tgggtaacgc      180
cagggttttc ccagtcacga cgttgtaaaa cgacggccag tgccaa                    226

<210> SEQ ID NO 23
```

```
<211> LENGTH: 203
<212> TYPE: DNA
<213> ORGANISM: Artificial Sequence
<220> FEATURE:
<223> OTHER INFORMATION: Right border Insert IND-115-7

<400> SEQUENCE: 23
attagggttc ctatagggtt tcgctcatgt gttgagcata taagaaaccc ttagtatgta      60
tttgtatttg taaaatactt ctatcaataa aatttctaat tcctaaaacc aaaatccagt     120
actaaaatcc agatccccg aattaattcg gcgttaattc agtacattaa aaacgtccgc     180
aatgtgttat taagttgtct aag                                              203

<210> SEQ ID NO 24
<211> LENGTH: 193
<212> TYPE: DNA
<213> ORGANISM: Artificial Sequence
<220> FEATURE:
<223> OTHER INFORMATION: Right flanking regions IND-115-7

<400> SEQUENCE: 24
gctaggaacg cttacgattg gcccttttgc cagcattccg atcaagctca ctatcagtca      60
acggttcgaa catgaaacaa tgcaaagtaa tcccaatcga tccaccttgt ttacgctgca     120
cagagaaacc caaattaaac tatgaacaat attttcttc accaacgtgc aaaagtacat     180
caatccaaca atg                                                         193

<210> SEQ ID NO 25
<211> LENGTH: 166
<212> TYPE: DNA
<213> ORGANISM: Artificial Sequence
<220> FEATURE:
<223> OTHER INFORMATION: Left flanking regions IND-13-4

<400> SEQUENCE: 25
cagcaatgca atgtatagaa agtaagtccc gtttgttagc aacttaatga gcttaatagg      60
actgagaact tattcggtca gctataaatg actgtgtggt agttggcttg atgatattga     120
aagtgactta ttcgttaaga tttacggggg agctttatgc agaaat                     166

<210> SEQ ID NO 26
<211> LENGTH: 199
<212> TYPE: DNA
<213> ORGANISM: Artificial Sequence
<220> FEATURE:
<223> OTHER INFORMATION: Left border insert IND-13-4

<400> SEQUENCE: 26
ccacagagtg ccatggcaac ccacagtaat tccagttacg gacttacata ccaagaaaag      60
gtaaaagcaa taagaaatat atgaaaatta gtccaccata aatcttatag tttatggttt     120
agggtaacac tctaacactc tactacatta cttatattta ctttaaacta tctataaaac     180
aatttaaaca tagtagaat                                                   199

<210> SEQ ID NO 27
<211> LENGTH: 145
<212> TYPE: DNA
<213> ORGANISM: Artificial Sequence
<220> FEATURE:
<223> OTHER INFORMATION: Right border insert IND-13-4

<400> SEQUENCE: 27
tatcaataaa atttctaatt cctaaaacca aaatccagta ctaaaatcca gatcccccga      60
```

-continued

```
attaattcgg cgttaattca gtacattaaa aacgtccgca atgtgttatt aagttgtcta    120
agcgtcaatt tgtttacacc acaat                                         145

<210> SEQ ID NO 28
<211> LENGTH: 185
<212> TYPE: DNA
<213> ORGANISM: Artificial Sequence
<220> FEATURE:
<223> OTHER INFORMATION: Right flanking regions IND-13-4

<400> SEQUENCE: 28
aaaaaaccgt cccaaacaaa atcttttccg tccttacaga ttaatccaca caaacatagg     60
acttaatgaa aaccaaccaa acaaccccta tttggtaagc ttctagggag gagctttata    120
caaaaagcca tgatttttcc tagcctaccc ctcccggtta caaacacgct aatttcatcc    180
acgaa                                                               185
```

TRANSGENIC SAFFLOWER EVENT STACK IND-1ØØØ3-4 X IND-1ØØ15-7 AND METHODS TO USE IT

REFERENCE TO APPENDIX [CD ROM/SEQUENCE LISTING]

The instant application contains a Sequence Listing TXT which has been submitted electronically in TXT format and is hereby incorporated by reference in its entirety. Said TXT copy, created on Jan. 20, 2023 is named "118991_PD758US_SEQ_LISTING_ST25.txt" and is 39,157 bytes in size.

FIELD OF THE INVENTION

The invention relates to the transgenic stacking of accumulated safflower through improvement IND-1ØØØ3-4×IND-1ØØ15-7, and its plants, parts of it and seeds. These events allow the production of bovine chymosin in the seeds of safflower plants. This invention also relates to methods for detecting the presence of such safflower events in a biological sample and provides the nucleotide sequence specific to each event.

BACKGROUND OF THE INVENTION

Bovine chymosin is the enzyme used in the dairy industry for the coagulation of milk in cheese production. Originally, this enzyme was extracted from the stomachs of lactating calves. Due to increased demand, health problems and the high cost of production, it has been produced in recombinant form in bacteria and fungi using fermenters for almost 20 years. Today, more than 80% of the chymosin used in cheese production is of a recombinant origin.

The use of plants as bioreactors for the production of recombinant proteins has been widely documented. One of the advantages of the production of recombinant proteins in plants is the ease of scaling up production by increasing the cultivated area. By means of genetic engineering, safflower plants to accumulate chymosin in their seeds can be generated. This process of obtaining transgenic safflower with high expression of bovine chymosin in its seed requires the generation of transgenic events, as well as their molecular and phenotypic characterization, to identify and select the event that expresses the highest possible amount of active enzyme. In order to maximize the market potential of extracting chymosin by means of conventional equipment, more than one event can be combined.

The selection of each event has both development stages in the laboratory and field and/or greenhouse tests, where conditions are controlled. Analysis of events over several years, at multiple locations representing a variety of environmental conditions, is necessary to select the event that meets the phenotypic, genetic and marketing traits required. The selected event(s) must be very stable with regard to the level of expression and activity of the enzyme desired. These increases in expression shall not be related to losses in yield or grain quality. The present invention presents such commercially suitable events that give rise to new advantageous features in the chymosin-producing safflower seeds. These selected events can then be used to introduce said traits into other genotypes using breeding methods to produce different varieties containing the desired trait and adapted to specific growing conditions.

DETAILED DESCRIPTION OF THE INVENTION

The present invention provides chymosin-producing safflower plants containing the event stack IND-1ØØØ3-4×IND-1ØØ15-7. These plants express the bovine enzyme chymosin in seeds allowing them to maintain their post-harvest catalytic activity while maintaining standard preservation conditions.

More specifically, the present invention refers to the safflower event stack designated as IND-1ØØØ3-4×IND-1ØØ15-7, which has a representative seed deposited on 10 Jul. 2020 with the American Type Culture Collection (ATCC) with access number PTA-126769 and the descendants derived from it.

The present invention includes, additionally, safflower plants comprising the molecular stacking of the events IND-1ØØØ3-4×IND-1ØØ15-7 represented by SEQ ID NO: 1 and SEQ ID NO: 2.

The transgenic inserts present in the molecular stack of the invention and in the registered seed comprise the following genes: one single copy of the selection marker gene pat and a single copy of the gene that codes for the enzyme chymosin cym, with a copy of each insert present in the molecular stack of events IND-1ØØØ3-4×IND-1ØØ15-7. The pat gene derived from *Streptomyces viridochromogeness* codes the protein PAT (Phosphinothricin Acetyl Transferase). The cym gene derives from *Bos taurus* sp. bovine and codes for the chymosin enzyme, which possesses aspartic protease activity with the ability to coagulate milk. Regulation of the genes of interest may be directed by various promoter sequences that have different levels of expression, sensitivity and tissue specificity. Subject-matter experts know that any nucleic acid promoter or terminator can be used to direct or regulate the expression of the gene of interest without altering the essence of the invention. In particular, the event developed in this invention contains the ubiquitin promoter (prUBI) and the terminator TerUBI for the gene pat, which confers resistance to the glufosinate-ammonium herbicide. On the other hand, the event contains the phaseolin promoter (prPHA) and the terminator TerPHA to regulate the expression of the codifying region of cym (FIG. 1) in each of its inserts.

Other aspects of the invention comprise the progeny of safflower plants, seeds, and/or regenerative parts of plants and seeds and progeny comprising the molecular stacking of safflower events IND-1ØØØ3-4×IND-1ØØ15-7, as well as food and feed derived therefrom. The invention also includes parts of plants comprising the molecular stacking of safflower events IND-1ØØØ3-4×IND-1ØØ15-7, including, but not limited to, pollen, eggs, flowers, buds, roots, leaves, nuclei of vegetative cells, and other plant cells comprising the molecular stack of safflower events IND-1ØØØ3-4×IND-1ØØ15-7. The invention further relates to safflower plants comprising the molecular stacking of safflower events IND-1ØØØ3-4×IND-1ØØ15-7 which express the chymosin enzyme in seeds.

This invention relates in part to the cultivation of enzyme-producing plants. In addition, it includes the novel molecular stacking of two transformation events in safflower plants comprising polynucleotides, as described herein, inserted at specific points within the safflower genome that confer particular genetic and phenotypic traits.

In some forms of realization, such events/polynucleotides may be "stacked" with other traits including, for example, agronomic, quality, and herbicide and/or insect tolerance traits. The present invention includes plants that have an individual event derived from stacking by crossing inserts with similar traits, as described herein.

Additional traits can be stacked in the plant genome or at the same locus as the molecular stack of safflower events IND-1ØØØ3-4×IND-1ØØ15-7, for example, through plant breeding, retransformation of the transgenic plant containing the molecular stack of safflower events IND-1ØØØ3-4×IND-1ØØ15-7, or addition of new traits thru the homologous recombination directed integration.

In a form of realization, the present invention comprises two genomic points of safflower. In some forms of realization, the directed point comprises a heterologous nucleic acid. Safflower genomic points are located between the flanking sequences established in SEQ ID NO: 3: (right junction region of IND-1ØØØ3-4), SEQ ID NO 4 (left junction region of IND-1ØØØ3-4), SEQ ID NO: 5: (right junction region of IND-1ØØ15-7), SEQ ID NO: 6 (left junction region of IND-1ØØ15-7).

In a form of realization, the present invention comprises a method for the production of transgenic safflower plants, involving inserting heterologous nucleic acids at specific positions in the genome.

In particular, the method comprises transforming a cell or a cellular culture in a stable form with the sequences ADN SEQ ID NO 7: insert and regenerate the cell giving rise to an entire plant.

The transformation of such a plant cell can be carried out through various techniques, whether physical, viral or chemical. Among them: bio-ballistics, electroporation, transformation by bacteria, or the combination of some of them. All of these techniques are well known to the knowledgeable person.

The invention further presents a microorganism comprising a nucleic acid molecule with a nucleotid sequence selected from the group SEQ ID NO: 1 and SEQ ID NO: 2.

In particular, this invention uses *Agrobacterium tumefaciens* transformed with the DNA molecule from SEQ ID NO 7, more precisely transformed with plasmid pSBS2165 (FIG. 1).

In addition, this invention provides tests for detecting the presence of the molecular stack of safflower events herein in a safflower sample. The tests may be based on the DNA sequence of the recombinant construct, inserted into the safflower genome, and on the genomic sequences flanking the insertion points. Kits and conditions that are useful in testing are also provided.

Therefore, the present invention relates in part to the cloning and analysis of the DNA sequences of all or part of the inserts and flanking regions (in transgenic safflower lines). These sequences are unique. On the basis of these inserts and the flanking (and bonding) sequences, it is possible to generate event-specific primers. The PCR technique showed that these events may be identified by analysis of the amplicons generated with these event-specific primer sets. Therefore, these and related procedures can be used to uniquely identify safflower lines comprising the events of the present invention.

This invention also relates in part to PCR tests. These include real-time qPCR or end-time PCR among others, for the detection of molecular stacking of safflower events IND-1ØØØ3-4×IND-1ØØ15-7, or each of them separately IND-1ØØØ3-4 and IND-1ØØ15-7, amplicons and fragments thereof.

The invention also presents DNA molecules comprising a sufficient length of the sequence of contiguous nucleotides of SEQ ID NO: 14 and 20 so that it works as a DNA probe that hybridizes, under rigorous hybridization conditions, to a DNA molecule comprising a sequence of nucleotides selected from the group consisting of SEQ ID NO: 1 and SEQ ID NO: 2, and that does not hybridize under rigorous hybridization conditions to a DNA molecule not comprising a sequence of nucleotides selected from the group consisting of SEQ ID NO: 1 and SEQ ID NO: 2.

In some cases, the probes used may be marked with molecules that emit a detectable signal. An example of such molecules is fluorochromes. That is to say, oligonucleotides that present fluorochromes at both ends and have a complementary sequence to part of the DNA fragment to be amplified. Among them are FAM, TET, HEX, JOE, CAL Fluor®, Quasar®, and Pulsar® dyes, among other.

The invention further discloses a pair of DNA molecules consisting of a first DNA molecule and a second DNA molecule different from the first DNA molecule, where each of the first and second DNA molecules comprises a sufficient stretch of contiguous nucleotides of SEQ ID NO: 1 and SEQ ID NO: 2: to function as DNA probes if used together in an amplification reaction with DNA derived from the molecular stacking of safflower events IND-1ØØØ3-4×IND-1ØØ15-7, to produce two diagnostic DNA amplicons of the molecular stack of transgenic safflower events IND-1ØØØ3-4×IND-1ØØ15-7 in one sample.

The invention further describes a method for detecting the presence of DNA obtained from the molecular stacking of safflower events IND-1ØØØ3-4×IND-1ØØ15-7 in one sample. The method involves checking the sample against the DNA molecules used as probe and primers, subjecting them to rigorous hybridization conditions, and detecting hybridization of the DNA probe to the DNA in the amplified sample, with the use of specific primers, where such hybridizations indicate the presence of DNA derived from the transgenic safflower event IND-1ØØØ3-4×IND-1ØØ5-7 in the sample.

The invention also presents a method for detecting the presence of DNA molecules obtained from the molecular stacking of safflower events IND-1ØØØ3-4×IND-1ØØ15-7, in one sample, by matching the DNA preparation derived from it with a pair of oligonucleotides used as primers to perform an amplification reaction sufficient to produce DNA amplicons comprising selected sequences from the group consisting of SEQ ID NO: 1 and SEQ ID NO: 2 and, by detecting the presence of DNA amplicons in the reaction, where the presence of DNA amplicons in the reaction indicates the presence of a DNA molecule derived from the molecular stacking of safflower events IND-1ØØØ3-4×IND-1ØØ15-7 in the sample.

The invention further presents a DNA detection kit comprising at least one DNA molecule with a sufficient amount of contiguous nucleotides of SEQ ID NO: 1 and SEQ ID NO: 2 to work as specific DNA primer or probe to detect the presence of DNA derived from the molecular stacking of safflower events IND-1ØØØ3-4×IND-1ØØ15-7, where the DNA detection is diagnostic of the presence of the molecular stack of safflower events IND-1ØØØ3-4×IND-1ØØ5-7 in one sample.

The invention further presents a safflower plant, seed, cell or part of such a plant comprising nucleic acid molecules having sequences SEQ ID NO: 1 and SEQ ID NO: 2. The invention further presents a safflower plant, seed, cell or part of a plant expressing chymosin. The invention further presents a safflower plant, seed, cell or part of a plant, the genome of which produces an amplicon comprising DNA molecules having sequences SEQ ID NO: 1 and SEQ ID NO: 2 when analyzed by a DNA amplification method.

The invention further presents a safflower plant or seed, where the safflower plant or seed is generated from the molecular stacking of safflower events IND-1ØØØ3-4×IND-1ØØ15-7, or each of them separately IND-1ØØØ3-4 and IND-1ØØ15-7, o is a hybrid or heterozygous that has at least one parent derived from the transgenic safflower event IND-1ØØØ3-4×IND-1ØØ15-7, c IND-1ØØØ3-4 and IND-1ØØ15-7.

The invention further presents non-living plant material comprising recombinant DNA molecules having sequences SEQ ID NO: 1 and SEQ ID NO: 2.

The invention further presents a consumer product produced as a consequence of the molecular stacking of safflower events IND-1ØØØ3-4×IND-1ØØ15-7, and comprising nucleic acid molecules selected from the group consisting of SEQ ID NO: 1 and SEQ ID NO: 2, where the detection of a nucleotide sequence in a sample derived from a consumer product is decisive for the consumer product to be derived from the molecular stacking of safflower events IND-1ØØØ3-4×IND-1ØØ15-7, or each of them separately IND-1ØØØ3-4 and IND-1ØØ15-7.

The invention further presents a method for producing a consumer product by obtaining a safflower plant or part thereof, comprising the molecular stacking of safflower events IND-1ØØØ3-4×IND-1ØØ15-7 and for producing a consumer product from a safflower plant or part thereof.

The invention presents a method for producing a safflower plant that produces the enzyme chymosin by crossing a plant with the molecular stacking of safflower events IND-1ØØØ3-4×IND-1ØØ15-7, or each of them separately IND-1ØØØ3-4 and IND-1ØØ15-7. The progeny resulting from the use of these methods can be varieties or hybrids, homozygotes or heterozygotes for IND-1ØØØ3-4 and IND-1ØØ15-7. Plants can be self-fertilized or crossed-fertilized. Plants with the events can be self-fertilized to produce inbred, genetically uniform, homozygous lines for IND-1ØØØ3-4 and IND-1ØØ15-7. Alternatively, the progeny can be cross-fertilized to produce varieties or hybrids. The seed of the progeny thus produced contains the events IND-1ØØØ3-4 and IND-1ØØ15-7 and may be used to obtain chymosin. The plants of the progeny can be analyzed using diagnostic methods or molecular markers that allow the identification of events IND-1ØØØ3-4 and IND-1ØØ15-7. In addition, these plants can be treated with glufosinate herbicide for selection.

BRIEF DESCRIPTION OF THE DRAWINGS

FIGS. 7A to 7D: T-DNA flanking sequences in events IND-1ØØØ3-4 and IND-1ØØ15-7. A) and B) Flanking sequences neighboring the left border (SEQ ID NO: 21 and 22) (LB) and right border (RB) (SEQ ID NO: 23 and 24), respectively, of event IND-1ØØ15-7. C) and D) Flanking sequences neighboring the left border (LB) (SEQ ID NO: 25 and 26) and right border (RB) (SEQ ID NO: 27 and 28), respectively, of event IND-1ØØØ3-4. The bases in red correspond to the safflower genome and the bases in black correspond to the T-DNA of each insert.

BRIEF DESCRIPTION OF THE SEQUENCES

Figure 1:
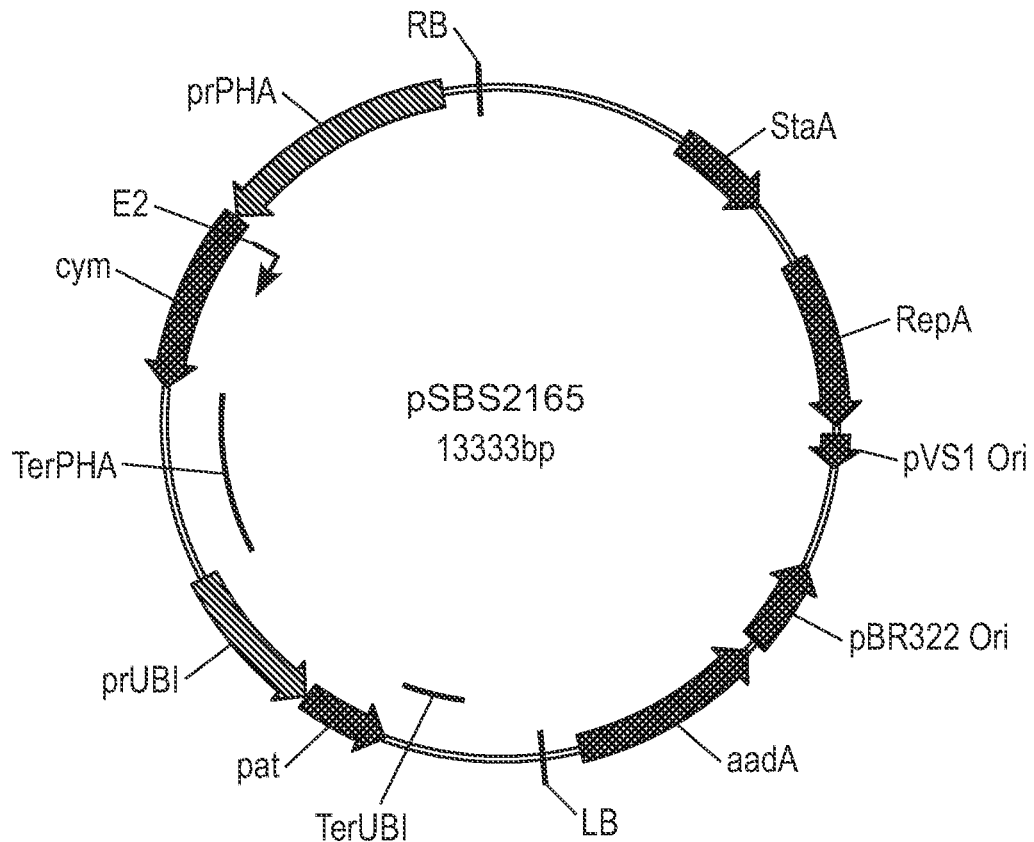
FIG. 1: Transformation vector diagram pSBS2165.

SEQ ID NO: 1 Representative sequence of the event IND-1ØØØ3-4. This sequence includes the genomic region 5' of the joint point, the complete insert and the genomic region 3' of the joint point.
SEQ ID NO: 2 Representative sequence of the event IND-1ØØ15-7. This sequence includes the genomic region 5' of the joint point, the complete insert and the genomic region 3' of the joint point.
SEQ ID NO: 3 Right splicing of the event IND-1ØØØ3-4.
SEQ ID NO: 4 Left splicing of the event IND-1ØØØ3-4.
SEQ ID NO: 5 Right splicing of the event IND-1ØØ15-7.
SEQ ID NO: 6 Left splicing of the event IND-1ØØ15-7.
SEQ ID NO: 7. Complete insert sequence.
SEQ ID NO: 8 primer 15.
SEQ ID NO: 9 primer 16.
SEQ ID NO: 10 primer 707.
SEQ ID NO: 11 primer 1170.
SEQ ID NO: 12 primer 656.
SEQ ID NO: 13 primer 13.
SEQ ID NO: 14 primer 1090.
SEQ ID NO: 15 probe 1091.
SEQ ID NO: 16 primer 716.
SEQ ID NO: 17 primer 1099.
SEQ ID NO: 18 primer 1546.
SEQ ID NO: 19 primer 1547.
SEQ ID NO: 20 probe 1548.
SEQ ID NO: 21 Left flanking regions IND-1ØØ15-7.
SEQ ID NO: 22 Left border Insert IND-1ØØ15-7.
SEQ ID NO: 23 Right border Insert IND-1ØØ15-7.
SEQ ID NO: 24 Right flanking regions IND-1ØØ15-7.
SEQ ID NO: 25 Left flanking regions IND-1ØØØ3-4.
SEQ ID NO: 26 Left border insert IND-1ØØØ3-4.
SEQ ID NO: 27 Right border insert IND-1ØØØ3-4.
SEQ ID NO: 28 Right flanking regions IND-1ØØØ3-4.

DETAILED DESCRIPTION

The following examples illustrate procedures for implementing the invention and to demonstrate certain preferred forms of implementation of the invention. Such examples should not be interpreted as restrictive. Technical experts should appreciate that the techniques disclosed in the following examples represent specific methods used to illustrate preferred modes of practice. However, in view of the present disclosure, technical experts should appreciate that various changes can be made to such specific forms of implementation while obtaining similar or like results without departing from the spirit and scope of the invention.

EXAMPLES

Example 1: Construction of Plasmid pSBS2165

Plasmid pSBS2165, which would later be used for the processing of safflower plants, is derived from the family of pPZP binary plasmids. In particular, it is based on the pPZP200 series.

The transgenic insert and the expression cassette present at the events IND-1ØØØ3-4 and IND-1ØØ15-7 includes the ubiquitin promoter (prUBI) and the terminator TerUBI for the pat marker gene. Additionally, it includes the promoter of the gene pha of *Phaseolus vulgaris* and the terminator TerPHA for the gene cym.

The resulting plasmid pSBS2165 is shown in FIG. 1.

Example 2: Transformation of Safflower Plants and Selection of the Molecular Stack of Safflower Events IND-1ØØØ3-4×IND-1ØØ15-7

The initial step in a transformation test is the preparation of bacterial suspensions of a strain of *Agrobacterium tumefaciens*, which carries the genes of interest and selection accompanied by the molecular sequences necessary for their expression in plants. These bacterial cultures are used as biological vectors for the transformation of plant cells and for the subsequent regeneration of transforming plants. For this, it is a requirement to maintain fresh colonies of *A. tumefaciens* at 28° C. on Petri dishes with semi-solid culture media added with selective agents (antibiotics for bacterial selection). From these colonies, bacterial cultures in liquid suspension are initiated for the infection of the transformation target explants.

The protocol developed in the processing and tissue culture laboratory defines as starting material to be used in processing trials the Centennial cultivar of Carthamus tinctorius, sections of cotyledon tissue obtained from pre-germinated seeds in sterility (5-6 days post-germination in darkness). These materials constitute totipotent explants, capable of de-differentiating and then regenerating safflower transgenic shoots under selective in vitro conditions. Once inoculated with *A. tumefaciens*, these explants constitute the starting material for in vitro regeneration of de novo transgenic plants.

The activities involved are described in stages below:

Surface Disinfection of Seeds and Obtaining Explants

The starting point in the transformation process is the surface disinfection of the safflower cv Centennial seeds. This process consists of washing the seeds in a diluted chlorine [11 g $Cl_2$/L] and detergent solution for 60 minutes, ending with three washes with sterile distilled water. The seeds are then left to incubate for 16 hours in an antibiotic and antifungal disinfectant solution (timentin [400 mg/L] and nystatin [125 mg/L]). Once this time has elapsed, the seeds are peeled and sown in a germination culture containing: 0.5×MS Medium, 10 g/L Sucrose and 8 g/L Agar, pH 5.8 in a Petri dish of 90 mm×25 mm for 5 days.

Transformation Procedure

The germinated seeds are selected and placed in a Petri dish with 5 mL of inoculation medium containing: 0.2×MS Medium, Glucose 10 g/L, Acetosyringone 100 uM, pH: 5.8.

Using a #11-scalpel blade, cuts were made in the cotyledons obtaining thin pieces of 1 mm width, which will be the actual transformation explants. These explants are then brought into contact with a suspension of *A. tumefaciens* and incubated in agitation for 30 minutes. Subsequently, the period of indirect co-cultivation of the explants in darkness begins for 5-6 days at 24° C. The co-cultivation medium contains 0.2×MS Medium, Glucose 10 g/L, Acetosyringone 100 uM and Agar 12 g/L pH: 5.8 in a 90 mm×25 mm Petri dish.

Selection and Regeneration of Transformed Explants

After co-culture, the explants are transferred to callus-inducing medium, whose composition is 1×MS Medium, 30 g/L Sacarose, 2 g/L Gelzan, TDZ 0.2 mg/L, ANA 0.5 mg/L, Timentin 200 mg/L, and Glufosinate ammonium 3 mg/L, pH 5.8 in a 90 mm×25 mm Petri dish. The material must be kept for 30 days in darkness at 24° C.

Then, the generated callus must be sub-cultivated in sprout inducing medium with a composition of: 1×MS medium, 30 g/L Sacarose, 2 g/L Gelzan, Kinentin 0.5 mg/L, 2 iP 1 mg/L, Timentin 200 mg/L, Cefotaxime 200 mg/L, Glufosinate ammonium 3 mg/L and pH 5.8 in a 90 mm×25 mm. Petri dish. The material must be maintained for 3 months by performing periodic sub-cultures every 21 days. At this stage, the photoperiod is 16:8 hours light/darkness at 24° C.

The obtained neoformations are replanted into a sprouts development medium containing 1×MS medium, 30 g/L Sacarose, 2 g/L Gelzan, BAP 0.1 mg/L, IBA 0.1 mg/L, Timentin 200 mg/L, Cefotaxime 200 mg/L, Glufosinate ammonium 3 mg/L and pH: 5.8 in a 90 mm×25 mm Petri dish. The material is kept at a photoperiod of 16:8 hours of light/darkness at 24° C.

Sprouts that reach a height greater than 1 cm are replanted into an elongation medium, which differs from the sprouting medium in that it does not carry growth regulators or selector agent and, the gelling agent is agar at a final concentration of 6 g/L. For this period, the necessary photoperiod is 10/14 hours of light/darkness at 24° C. As in the previous instances, the material must be sub-cultivated every 21 days in 400 cm$^3$ glass containers.

Ex Vitro Hardening and Rooting

When the shoots generated in vitro reach a height of approximately 6-7 cm, they are hardened off. For this process, it is necessary to autoclave-sterilize the mixed substrate at 121° C. for 80 minutes.

At the time of hardening, the film covering the jars is removed by extracting the elongated shoots, which are washed at their basal end under running water. Immediately a perpendicular cut is made on the stem, a few millimeters above the base, adding a rooting solution (Dip'n&grow) for 1 minute. After this time, the sprouts are sown in 180 cm$^3$ containers perforated at its base, containing the sterile mixed substrate. The containers containing the sprouts are placed inside transparent plastic pots of approximately 1.2 L with 20-25 cm$^3$ water and are covered with 2 layers of film to keep the humidity inside. The material is kept in chambers under controlled conditions: photoperiod of 10-14 hours of light/darkness, 24° C. temperature and light intensity of 9500-10500 lux.

Acclimatization

Those plants that successfully overcome the rooting period are transplanted into larger pots using the same sterile mixed substrate that was used in the hardening. In this instance, the specimens are generally in a position to be molecularly characterized by PCR. For this purpose, leaf tissue samples are taken in 2 mL microtubes. After the molecular analysis, the transgenic events can be identified, that is, those specimens that are positive for the transgene of interest.

Such transgenic events will receive a unique traceability ID and must be maintained under controlled conditions until full harvest of $T_1$ seeds.

Pre-Selection of Events

Eighty-two transgenic safflower events derived from different *agrobacterium*-mediated transformation trials and different molecular expression strategies were evaluated. For all three strategies, the centennial safflower variety was used in the transformation experiments. T1 seeds were obtained for all independent events. The first multiplication of the transformed plants was carried out in a greenhouse and T1 individuals derived from each event were sampled for a Mendelian segregation test by PCR determination. After these analyses, the non-segregated Mendelian lines were discarded. Lines derived from self-pollinations of individuals from selected events (Mendelian segregation 3:1 in T1) were chosen. Phenotypes with different traits were identified during the growing season, scored and discarded. In order to identify homozygous lines, the plants were sampled for PCR analysis during the vegetative stages. The increase of seeds (T3 seeds) of homozygous and null lines was carried out in a greenhouse. Additionally, the level of expression of the cym gene on homozygous lines was evaluated by transcriptional expression analysis. For this purpose, the transcripts corresponding to T2 achenes from transgenic T1 plant chapters obtained with three different molecular expression strategies were detected and quantified. In most cases, one chapter per plant and three plants per transgenic event (i.e., three chapters per event) were taken. As a negative expression control, Centennial plant achenes were taken. Samples were taken from mature achenes and RNA was extracted from seed pools from the same chapter (using the RNeasy Plant Mini Kit QIAGEN commercial kit). The integrity of the purified RNA is assessed by running 5 μL of each sample in an agarose gel at 1% in TAE buffer. Once the integrity of these was corroborated, the quantification was carried out using the Quant-iT™ RiboGreen® RNA Assay kit. Then, 2 μg RNA from each sample was treated with DNase I to remove possible traces of genomic DNA (gDNA) that may have remained during the extraction. In order to corroborate the DNase treatment, a final time PCR was performed using specific oligonucleotides for the FAD2-1 gene. A PCR reaction for an endogenous safflower gene was then performed on the RNA samples to rule out DNA contamination. Finally, using Oligo dT, the reverse transcription was performed. The synthesized cDNAs were diluted and used for real-time PCR analysis of the expression level of the gene of interest, using appropriate controls. The expression of the gene of interest was analyzed using FAD2-1 as a standardizing gene. Of the three molecular expression strategies evaluated, one yielded results that allowed us to rule out the events obtained due to null chymosin expression levels.

To continue the selection, 22 transgenic safflower events belonging to two different molecular strategies were evaluated under field conditions. Evaluations were made of seed quantity and quality, as well as the level of activity of the chymosin recovered from the seeds.

Using as a last selection criterion the level of activity of recovered chymosin, two homozygous lines belonging to 2 different events were selected. Both events derive from the same transformation test with the same molecular expression strategy.

Selection of Events IND-1ØØØ3-4 and IND-1ØØ15-7 and Stacking to Allow Purification of Chymosin with Standard Equipment Among the events obtained in the first stages of the project, a preliminary selection was made, discarding those events that showed agricultural penalties or lack of expression and activity of chymosin.

From these considerations, two events were selected: the transgenic safflower event IND-1ØØØ3-4 and the transgenic safflower event IND-1ØØ15-7.

As of 2008, IND-1ØØØ3-4 and IND-1ØØ15-7 safflower transgenic events began to be evaluated, mainly with regard to the expression and activity of chymosin in seeds, stability and other useful parameters.

To quantify the level of chymosin expression in the seeds, the coagulating capacity of milk in extracts from the different grain samples was analyzed. This clotting activity is expressed as IMCU/mL (International Milk Clotting Units per milliliter of tested solution) and the chymosin mass per gram of safflower seed.

Materials and Methods

The safflower grains were macerated in a mortar (0.1 gr/mL of extraction buffer $NaH_2PO_4$ 50 mM, NaCl 1.2 M, pH=6) at room temperature. After centrifugation at 11,000×g for 20 minutes, the supernatants obtained were used to measure the clotting activity.

Chymosin activity was measured following the method recommended by the International Dairy Federation (IDF 157, ISO 11815). Svelty milk powder (low heat, low fat) dissolved in a $CaCl_2$ 4.5 mM (0.11 gr/mL) solution was used as a substrate. An aliquot (500 µL) of the seed extract or a universal standard solution (CHR Hansen, 5 mg/mL in sodium acetate 73.5 mM, pH=5.5) was added to 25 mL of substrate preheated at 32° C. and incubated at this temperature in a continuously rotating water bath. The clotting time (in seconds) was used to calculate the activity using the formula: $t_{ref} \times c_{ref} \times a_{ref}/t_m$. Where:

$t_{ref}$=pattern clotting time, $c_{ref}$=universal standard concentration (in g/mL), $a_{ref}$=standard original activity (in IMCU: International Milk Clotting Units/gr) and $t_m$=sample clotting time.

In order to transform the values of the enzymatic activity into chymosin mass, the value of the intrinsic clotting activity of chymosin expressed in safflower seeds was used (SPC—Safflower Produced Chymosin). To this end, the specific activity (IMCU/mg) in 13 pure SPC preparations and the total protein concentration were determined. With these results, the specific activity (Ae) of SPC (109 IMCU/mg) was calculated.

Seed extracts from non-transgenic safflower showed no clotting activity (data not shown).

Results

The methodology used to obtain these transgenic events causes random insertion anywhere in the plant's genome. Accordingly, it is extremely unlikely that the inserts of different events are in the same place on the genome. The different location would make it possible for the conventional crossing of plants with two different insertion events to result in a stack that expresses greater clotting activity in its seeds than either of its parents. To this end, progress was made with the transgenic safflower event IND-1ØØØ3-4 and the transgenic safflower event IND-1ØØ15-7.

In order to analyze the result of this process, the chymosin activity in seeds of the transgenic safflower event IND-1ØØØ3-4, the transgenic safflower event IND-1ØØ15-7 and the product of its stacking, molecular stacking of safflower events IND-1ØØØ3-4×IND-1ØØ15-7 was measured again.

Figure 2:
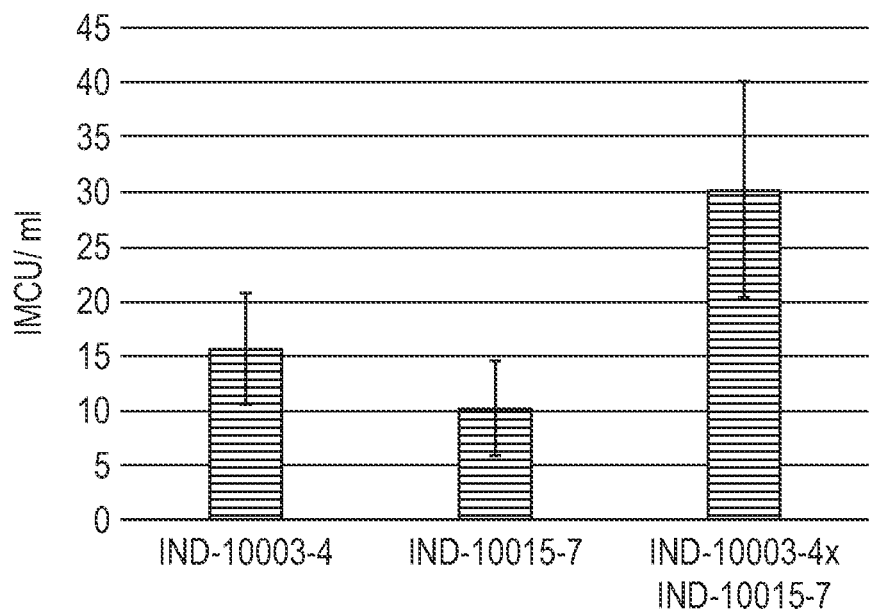
FIG. 2: Clotting activity. The ability to coagulate milk from seed extracts was measured from the transgenic safflower event IND-1ØØØ3-4, from the transgenic safflower event IND-1ØØ15-7, and from the stacking IND-1ØØØ3-4×IND-1ØØ15-7.
Figure 3:
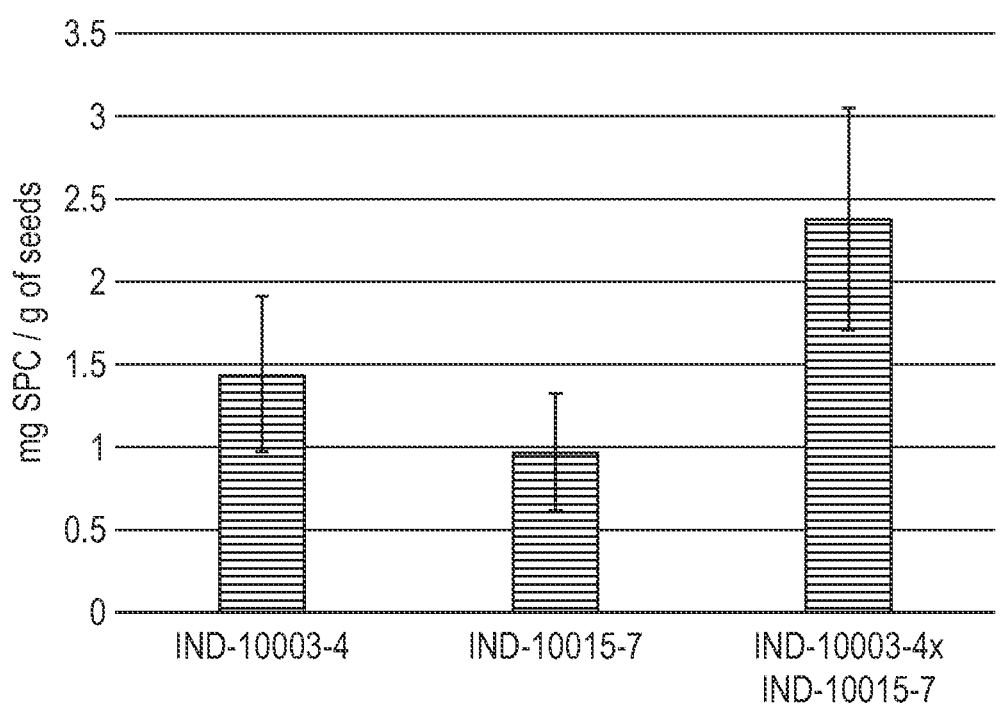
FIG. 3: Content of chymosin. The bovine chymosin content in seeds was determined from the transgenic safflower event IND-1ØØØ3-4, from the transgenic safflower event IND-1ØØ15-7, and from the product of its stacking (IND-1ØØØ3-4×IND-1ØØ15-7).

The result of the stacking of the two transgenic safflower events (IND-1ØØØ3-4×IND-1ØØ15-7) contains in its seed more clotting activity and more chymosin than its parental lines (FIGS. 2 and 3). These results confirm that the stacking yielded a more efficient and profitable variety of transgenic safflower for the purification of chymosin, a criterion used for the selection of the transgenic safflower IND-1ØØØ3-4×IND-1ØØ15-7.

Example 3: Characterization of the DNA Sequences of the Safflower Event IND-1ØØØ3-4×IND-1ØØ15-7

The molecular characterization of transgenic safflower plants with both insertion events, belonging to the molecular stack of safflower events IND-1ØØØ3-4×IND-1ØØ15-7, obtained by crossing IND-1ØØØ3-4 and IND-1ØØ15-7, was carried out using Southern blot and molecular biology techniques involving the amplification of specific DNA fragments by polymerase chain reaction and, in some cases, their subsequent sequencing.

Analysis of the Number of Copies of Coding Regions of Interest

By means of Southern blot, the number of copies present both in the separate events and in the product of their crossing was determined, thus determining the presence of only one copy of the cym gene of interest, and another in the same locus of the pat companion, using probes that hybridize with these particular regions.

Figure 4A:
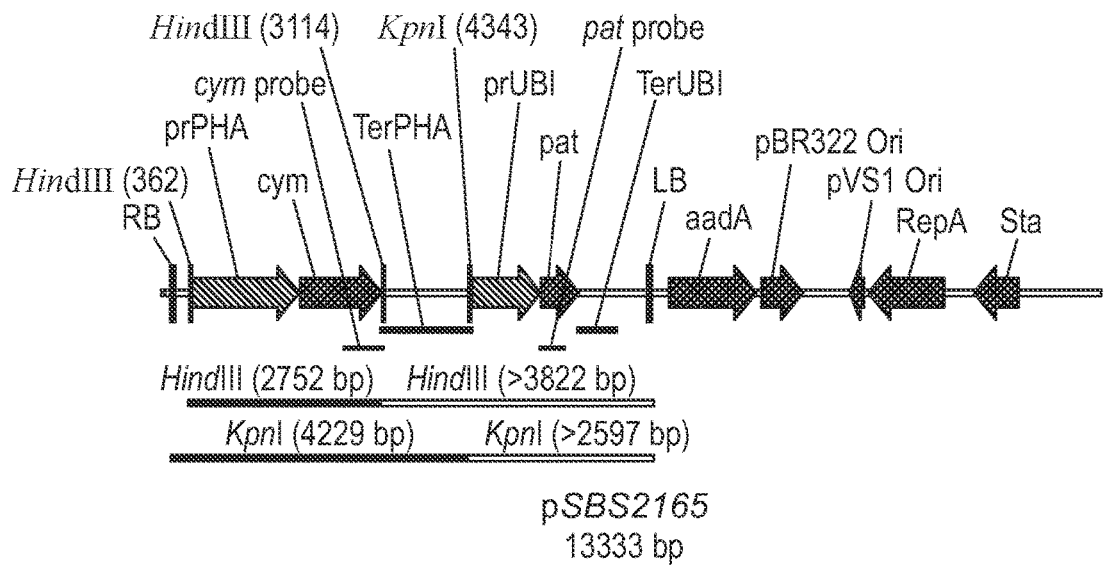
FIGS. 4A and 4B: Sequence diagrams involved in the transformation process. A) Linear plasmid map pSBS2165. B) Diagram of expected T-DNA insertion. In both diagrams, restriction points and probes used for event analysis are highlighted by Southern Blot (cym and pat, green horizontal lines) and the flanks of the joint point corresponding to the safflower genome (red boxes). The horizontal red lines indicate the fragments obtained by digesting genomic DNA with HindIII or with KpnI, and hybridizing with a cym probe. The horizontal blue lines indicate the fragments obtained by digesting genomic DNA with HindIII or with KpnI, and hybridizing with a pat probe.
Figure 4B:
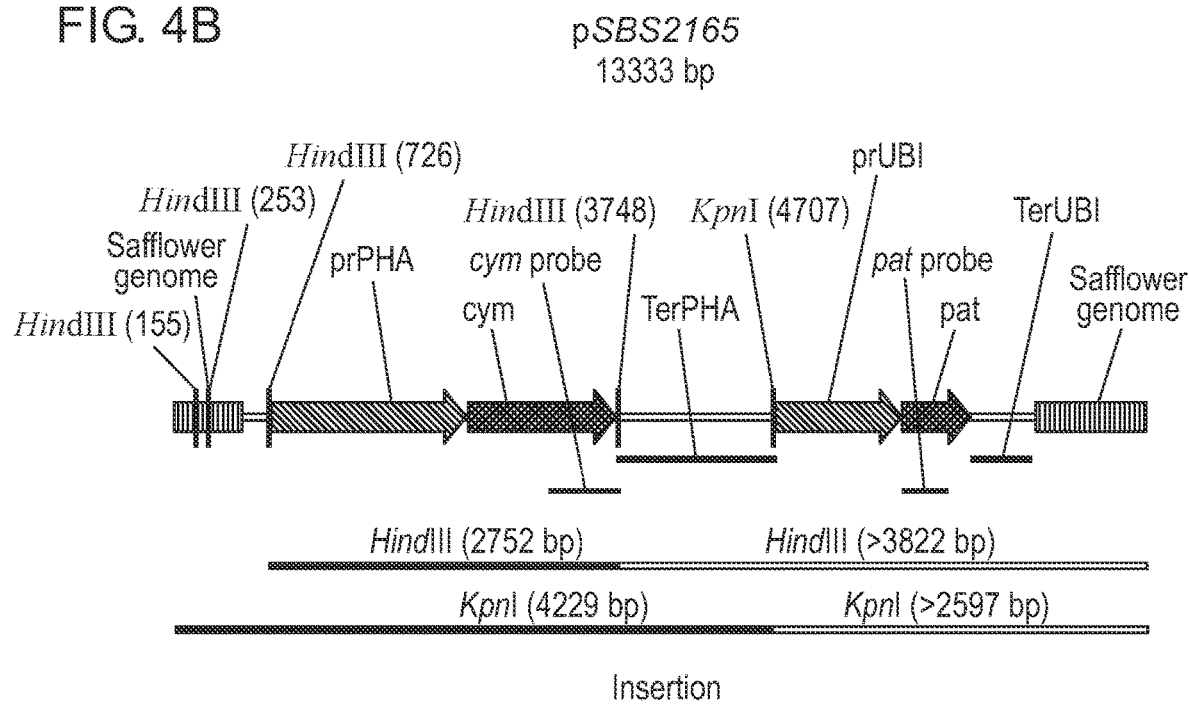

The digestion of the genomic DNA prior to the electrophoretic run was done with the HindIII and KpnI enzymes. There are two restriction sites of HindIII enzyme in the T-DNA of the construct used to originate the transgenic events (FIG. 4).

The cym hybridizing probe detected a single band of the expected size (2752 bp) in the streets corresponding to the genomes of IND-1ØØØ3-4, IND-1ØØ15-7 and IND-1ØØØ3-4×IND-1ØØ15-7 digested with HindIII. This would indicate the absence of major re-arrangements in the region comprising the cym coding region and the promoter that digests its expression, prPHA. On the other hand, when the genomic DNA was digested with KpnI, a band could be observed at each of the insertion events, IND-1ØØØ3-4 and IND-1ØØ15-7, of a size greater than 4229 bp, originated from the only cutting site present in the T-DNA and the closest site present in the plant's genome. Both bands are sufficiently different in size from each other and, as expected, could also be detected in the event IND-1ØØØ3-4×IND-1ØØ15-7. No bands were detected on the streets corresponding to the Centennial non-GM parent.

As for the pat probe, when digesting genomic DNA with HindIII, a band was detected for each event IND-1ØØØ3-4 and IND-1ØØ15-7, both of a size greater than 3822 bp of the expected minimum. These same bands were detected in the event originated by crossing IND-1ØØØ3-4×IND-1ØØ15-7. A similar result was obtained by digesting genomic DNA with KpnI.

Detection of Non-T-DNA Sequences

The verification of the absence of undesired plasmid sequences in transgenic events was performed by PCR with different combinations of oligonucleotides. These oligonucleotides were designed to amplify segments covering the entire plasmid region pSBS2165 outside the T-DNA, that is, that hybridize with the region that is not desired.

Figure 5A:
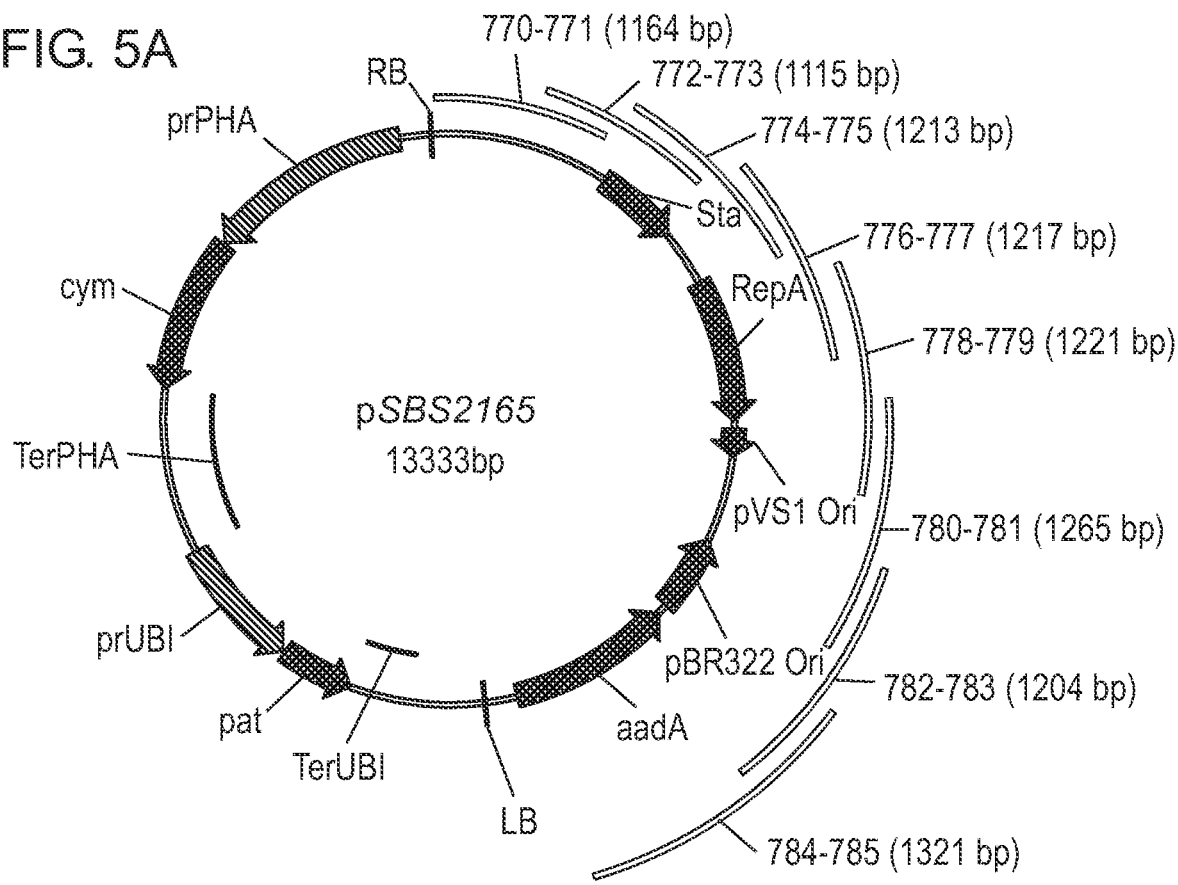
FIGS. 5A and 5B: Diagram of the amplified segments for the analysis of the presence of non-T-DNA plasmid regions in events IND-1ØØØ3-4 and IND-1ØØ15-7. A) Overlapping fragments, green lines indicate segments greater than 1000 bp amplified with each set of initiating oligonucleotides. Each segment indicates the initiating oligonucleotides used and the size of the amplicons in parentheses. B) Non-overlapping fragments, green lines indicate segments between 400 and 600 bp amplified with each set of initiating oligonucleotides. In each segment, the initiating oligonucleotides used and the size of the amplicons are indicated in parentheses.
Figure 5B:
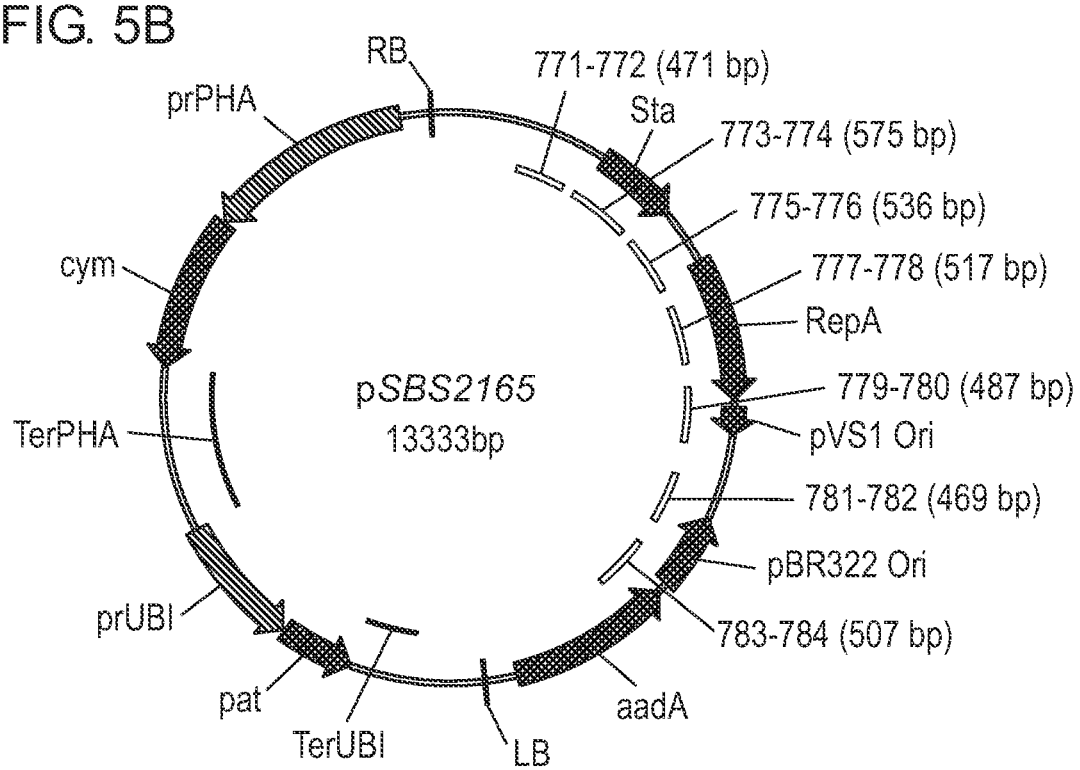

For the latter procedure, two series of initiating oligonucleotides were designed to amplify overlapping regions of approximately 1200 bp (FIG. 5A) and 500 bp (FIG. 5B) located outside the T-DNA region.

Figure 6:
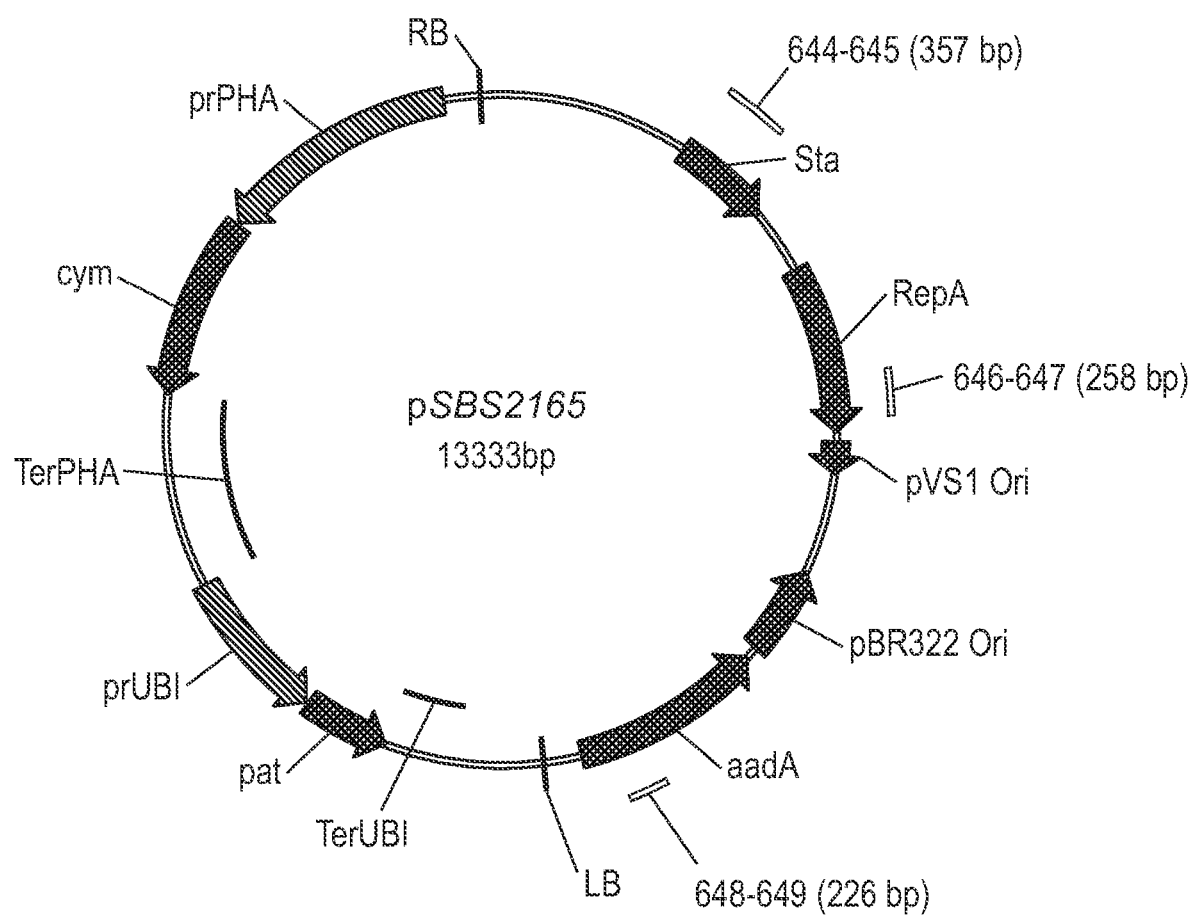
FIG. 6: Diagram of the amplified segment for the analysis of the presence of main non-T-DNA vector regions in events IND-1ØØØ3-4, IND-1ØØ15-7 and IND-1ØØØ3-4×IND-1ØØ15-7. The green lines indicate the amplicons of the main elements tested: sta, rep and aadA.

According to the results obtained, it can be expected that in the events IND-1ØØØ3-4 and IND-1ØØ15-7 there are no sequences of the plasmid pSBS2165 outside the T-DNA region, and the same would occur in the product of its crossing IND-1ØØØ3-4×IND-1ØØ15-7. The latter was also confirmed by the amplification of key regions of the plasmid used (FIG. 6) where no amplification products were observed.

Identification of Insertion Sites and Flanking Sequences

In order to identify the insertion site in the T-DNA genome, known sequences of the T-DNA were used to design oligonucleotides that amplify in the direction of the unknown flanking sequences. The Tail-PCR (Thermal Asymmetric Interlaced) technique was used to characterize both insertion sites of event IND-1ØØ15-7 and the closest flank to the left border (LB) of T-DNA of event IND-1ØØØ3-4. However, using this technique, it was not possible to amplify and isolate the other flank of IND-1ØØØ3-4, that is, the closest to the right border (RB) of T-DNA.

FIGS. 7 A, B and D show the sequences of the three flanks identified by Tail-PCR. In the flanks corresponding to IND-1ØØ15-7 the insert was determined to be in a gene that would code for an enzyme with glycoside hydrolase function. On the other hand, the flank identified of IND-1ØØØ3-4 suggested that the insert occurred in a gene region that would code for a hypothetical protein with chaperone function. Due to the lack of a fully assembled Carthamus tinctorious genome, in both cases the highest homology was found with probable coding regions of the *Cynara cardunculus* var. *scolymus* genome.

Due to the impossibility of determining the sequence of the remaining flank of the event IND-1ØØØ3-4 by Tail-PCR, attempts were made thru the specific amplification of the corresponding gene region with specific oligonucleotides. To do this, it used the sequence of the previously identified flank and the safflower transcriptome. This way, it was possible to identify the messenger RNA, transcribed by the gene interrupted by the T-DNA.

In the first instance, with oligonucleotides that hybridize at opposite ends of the transcript, the region corresponding to the untransformed Centennial genome was amplified by identifying the presence of an intron in the region of insertion. Next, with the gene sequence of interest now complete, progress was made in identifying the remaining flank of IND-1ØØØ3-4. This was done by PCR amplifications using oligonucleotides that targeted the corresponding T-DNA region (RB) and others in the opposite direction that hybridize over this T-DNA region.

However, PCR reactions using oligonucleotides that hybridized in the region adjacent to the RB of the T-DNA, corresponding to the phaseolin promoter sequences and the chymosin-coding region, were not successful. The latter raised the suspicion of a rearrangement in this region. Therefore, amplification was attempted with the use of oligonucleotides that hybridized in other regions of the T-DNA, in the expected or reverse direction. By means of this strategy, it was possible to identify a rearrangement in the T-DNA adjacent to the RB that comprises a fragment of the inverted phaseolin promoter and, adjacent to the intron previously detected in the safflower genome. These results made it possible to elucidate the sequence of the missing flank in the event IND-1ØØØ3-4 (FIG. 7C).

Segregation Analysis

As it is an event coming from a stack of events with independent inserts, the segregation analyses of both events were carried out by means of specific detection systems on the products of the crossing of homozygous individuals of IND-1ØØØ3-4 and IND-1ØØ15-7. In both cases, the DNA sequence inserted in the transformation events segregates the Mendelian way. This point details the studies carried out on F2 of the progeny obtained from the selfing of F1 from the mentioned crossing.

Figure 8A:
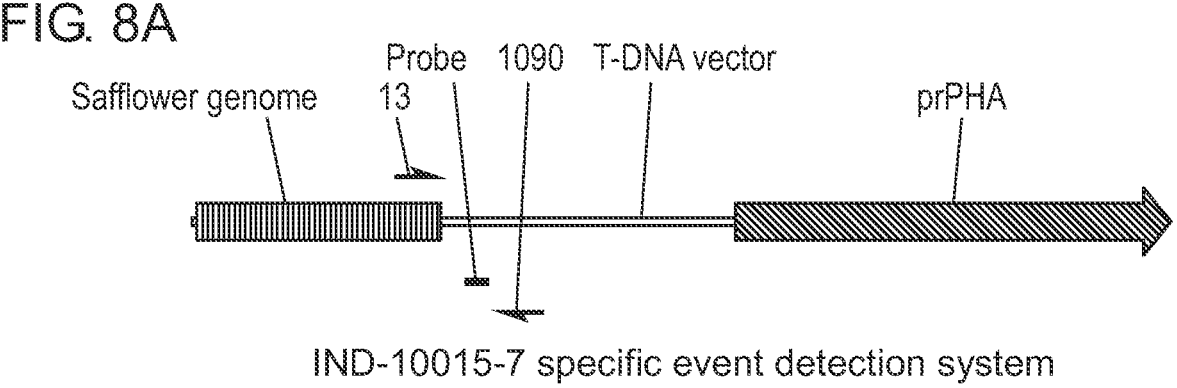
FIGS. 8A to 8D: Diagrams of event-specific detection system of event IND-1ØØ15-7×IND-1ØØØ3-4 and corresponding non-GM alleles (WT). A) Event-specific detection system of IND-1ØØ15-7. Diagram of the genome-flanking region neighboring the RB of T-DNA and part of the prPHA. The position of the oligonucleotides and the probe used to detect the event is indicated in real time and specifically by PCR. B) Diagram of the locus at Centennial (WT). The position of the oligonucleotides used to detect the wild allele corresponding to IND-1ØØ15-7 is indicated in real time by PCR. C) Event-specific detection system of IND-1ØØØ3-4. Diagram of the genome-flanking region neighboring the RB of the T-DNA and part of the TerUBI. The position of the oligonucleotides and the probe used to detect the event is indicated in real time and specifically by PCR. D) Diagram of the locus at Centennial (WT). The position of the oligonucleotides used to detect the wild allele corresponding to IND-1ØØØ3-4 is indicated in real time by PCR. The green lines indicate the position and size of the amplicons obtained by PCR.
Figure 8B:
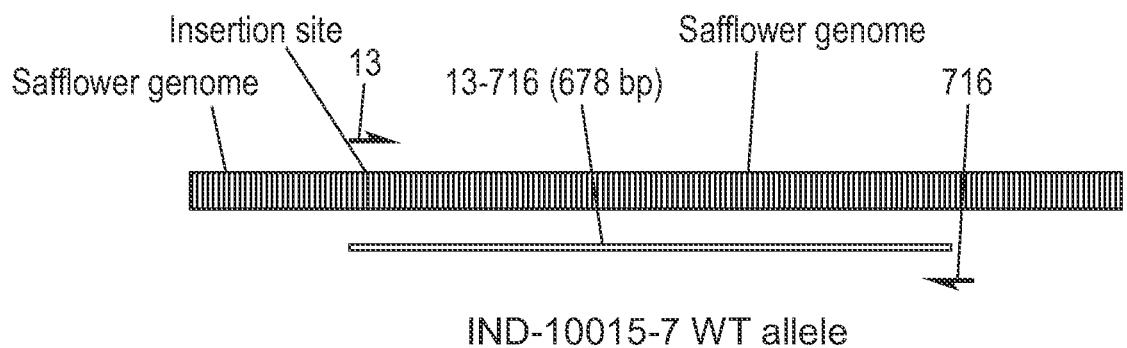
Figure 8C:
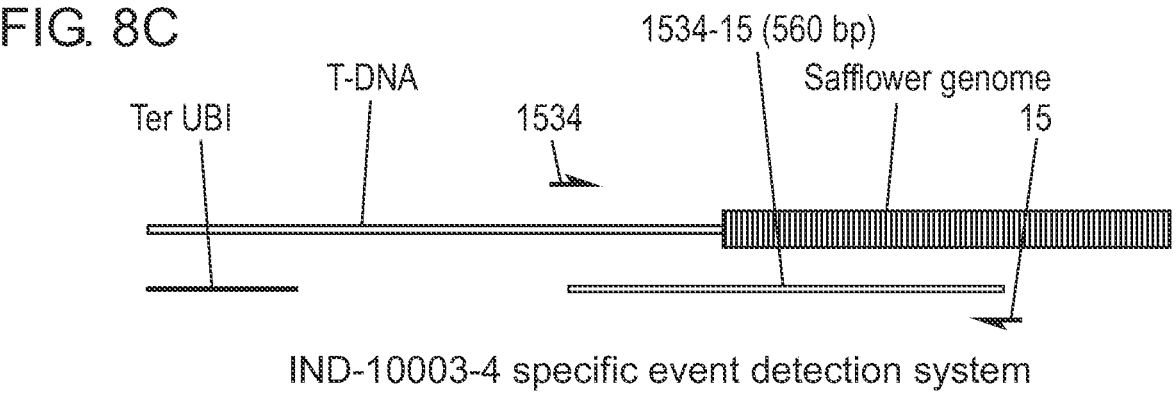
Figure 8D:
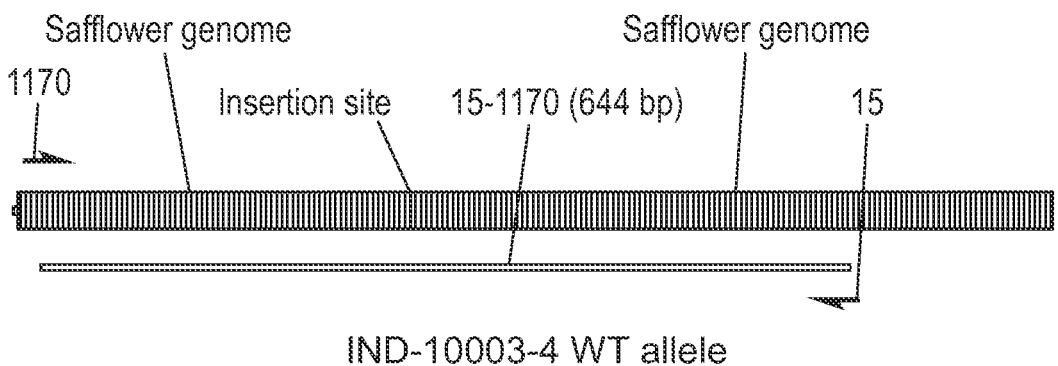

FIG. 8 shows the different fragments amplified by PCR, and the oligonucleotides used to detect the presence of the specific inserts of events IND-1ØØ15-7 and IND-1ØØØ3-4, FIGS. 8A and C of the specific event systems respectively. In addition to this, the diagrams corresponding to the regions of the unmodified safflower genome where the above-mentioned inserts were produced, FIGS. 8 B and D respectively, and the oligonucleotides used to detect these regions can be seen.

As a whole, these detection systems make it possible not only to detect the presence or absence of insertion events, but also the presence of unmodified regions and, therefore, to determine the zygosity of the individuals analyzed.

All these elements were used in the segregation studies carried out and in obtaining the molecular stacking of safflower events IND-1ØØØ3-4×IND-1ØØ15-7.

In addition to detecting specific sequences of each insertion event, the coding regions of interest common to both cym and pat were detected, thus confirming that these segregate linked to each other and to the other elements detected in this analysis, i.e. the joint points (insertion sites) and their flanking regions.

The results obtained are detailed in Table 1. The plants were classified as Homozygous, Hemizygous or non-GM according to the results obtained from the detection of the specific joint points of IND-1ØØØ3-4 and IND-1ØØ15-7 and their corresponding wild type alleles.

A Chi-square test ($\chi^2$) of each insert was performed to evaluate the expected 1:2:1 genotypic segregation (Homozygous:Hemizygous:non-GM) in an F2 population for each of the events, IND-1ØØØ3-4 and IND-1ØØ15-7.

The Chi-square test is based is based on the comparison of observed frequencies with expected frequencies according to Mendelian principles of inheritance. The $\chi^2$ statistics was calculated as:

$$\chi^2 = \Sigma[(O-E)2/E]$$

where O=frequency observed of genotype and E=frequency expected of genotype. An $\alpha$=0.05 and 2 degrees of freedom were used. The results of this analysis for each intervening event are detailed in Table 1.

TABLE 1

Results obtained in the $\chi^2$ test for the events IND-1ØØ15-7 and IND-1ØØØ3-4 in the 241 F2 plants analyzed. TR: transgenic locus. Non-GM: non-genetically modified locus

| Event | Genotype | Expected Result (N° of plants) | Expected Result (N° of plants) | $\chi^2$ 0.95 | Statistic Value |
|---|---|---|---|---|---|
| IND-1ØØ15-7 | Homozygous (+/+) TR/TR | 60 | 48 | 5.99 | 0.159 |
|  | Hemizygous (+/−) TR/Non-GM | 120 | 125 |  |  |
|  | Homozygous (−/−) Non-GM/Non-GM | 60 | 68 |  |  |

TABLE 1-continued

Results obtained in the $\chi^2$ test for the events IND-1ØØ15-7 and IND-1ØØØ3-4 in the 241 F2 plants analyzed. TR: transgenic locus. Non-GM: non-genetically modified locus

| Event | Genotype | Expected Result (N° of plants) | Expected Result (N° of plants) | $\chi^2$ 0.95 | Statistic Value |
|---|---|---|---|---|---|
| IND-1ØØØ3-4 | Homozygous (+/+) TR/TR | 60 | 57 | 5.99 | 0.829 |
| | Hemizygous (+/−) TR/Non-GM | 120 | 125 | | |
| | Homozygous (−/−) Non-GM/Non-GM | 60 | 59 | | |

The values of $\chi^2$ were less than 5.99 (gI=2, α=0.05) thus indicating no statistically significant difference between the observed and expected results under the Mendelian segregation 1:2:1 for the analyzed data.

Post-Crossing Integrity and Stability

To verify that the insertion and T-DNA remain unaltered over generations, after the stacking of both events their complete sequence, between one insert site and another, was characterized in segregating F2 individuals for each of the insert events, IND-1ØØØ3-4 or IND-1ØØ15-7. Therefore, these plants result from the selfing of F1 from crossing between homozygous individuals of events IND-1ØØØ3-4 and IND-1ØØ15-7. Thus, while in F1 both inserts are present in all plants, constituting the molecular stack of safflower events IND-1ØØØ3-4×IND-1ØØ15-7, after segregation in F2 the presence of only one of the inserts is detected in some plants, and these are the ones used in the present study.

In general, technically this was done by overlapping amplicons and sequencing them with Sanger on six F2 plants, which, as previously mentioned, had the insert of only one of the events, IND-1ØØØ3-4 or IND-1ØØ15-7. In these plants, the nucleotide sequences of both the inserts and their flanks were verified.

Analysis of Integrity and Identity Between the Sequences Present in the Molecular Stack of Safflower Events IND-1ØØØ3-4×IND-1ØØ15-7 and the T-DNA of Plasmid After the sequences of insertion events present in the molecular stack of safflower events IND-1ØØØ3-4×IND-1ØØ15-7 were verified, these were compared with the T-DNA sequence corresponding to the plasmid pSBS2165 used in the transformation and obtaining process of the transgenic safflower plants expressing CYM and PAT.

Figure 9:
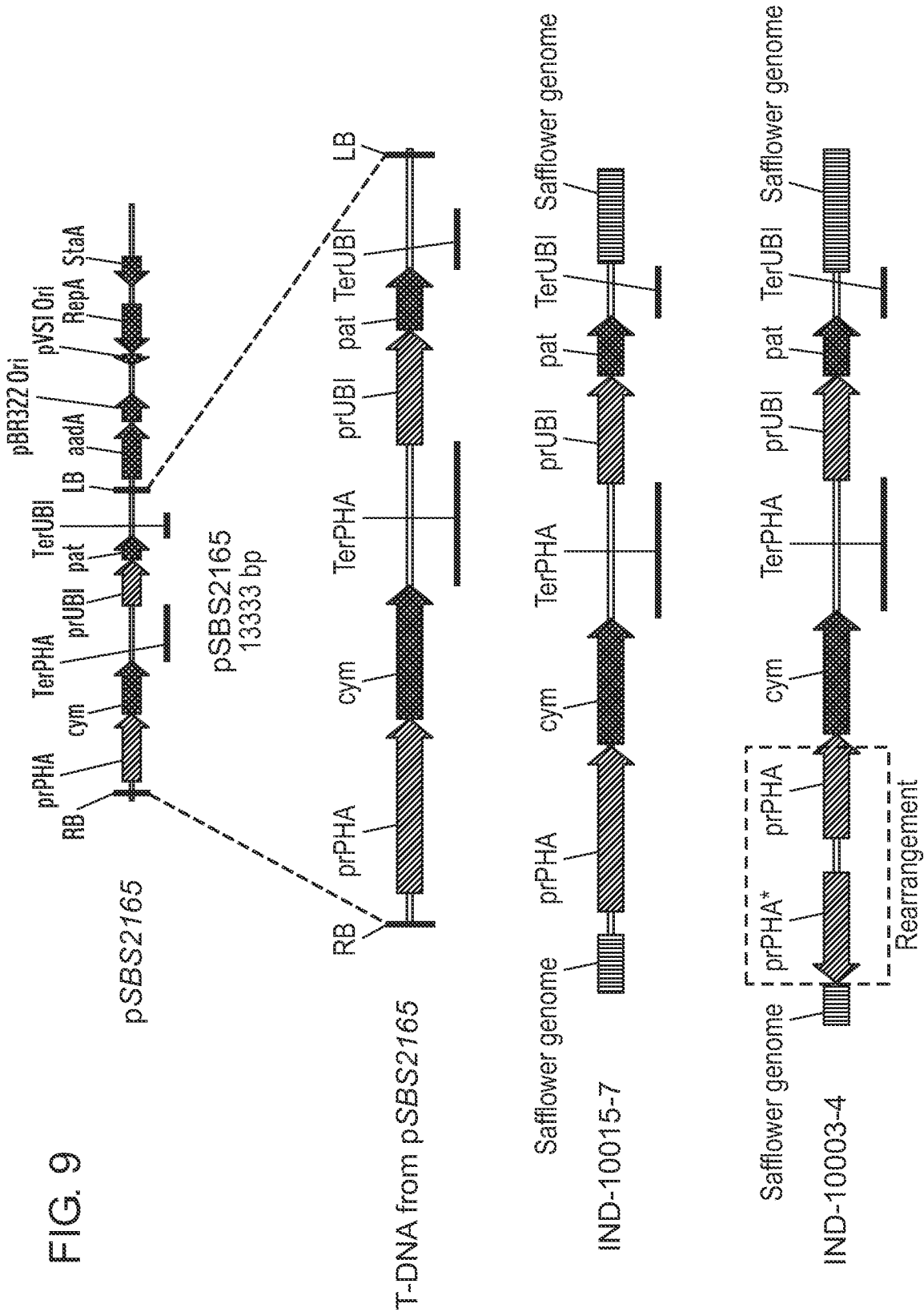
FIG. 9: Comparison between the maps of the T-DNA region and the inserts of the events IND-1ØØ15-7 and IND-1ØØØ3-4. Expression-promoting regions at the transcriptional level in green boxes, protein-coding regions in orange boxes and flanking regions in red boxes. The blue lines indicate the terminators at the transcriptional level. In the event IND-1ØØØ3-4, the region involving a re-arrangement is indicated in a fuchsia box: prPHA*, inverted and incomplete phaseolin promoter. prPHA, incomplete phaseolin promoter in the right direction.

FIG. 9 shows that while in the insert in IND-1ØØ15-7 the T-DNA sequence of the plasmid remained practically unchanged, in the insert corresponding to IND-1ØØØ3-4 changes involving the phaseolin-promoting region are detected.

The phaseolin promoter (prPHA) in the plasmid used in the transformation directing the expression of the CYM coding region is made up of 1547 bp. The re-arrangement detected in IND-1ØØØ3-4 led to the insert of 1064 bp upstream the transcription start site and, reversely, it was called prPHA*. In addition, the sequence of the prPHA promoter directing the expression of cym was detected to be a shorter version of active 1005 bp and is properly located regarding the above-mentioned coding region.

Stability of Stacked Events in Successive Generations of Selfing

Once the information is obtained indicating that in F2 individuals from the crossing between IND-1ØØØ3-4 and IND-1ØØ15-7 the inserts were intact and stable with respect to the parents, their stability was analyzed over successive generations of selfing of plants from the molecular stack of safflower events IND-1ØØØ3-4×IND-1ØØ15-7.

To this end, individuals belonging to homozygous lines of generations F4, F6 and F8 were selected and the presence of the main elements of interest was detected. These regions included the coding regions of cym and pat, and useful sequences for event-specific detection that include flanking regions, both right and left for both events.

Figure 10A:
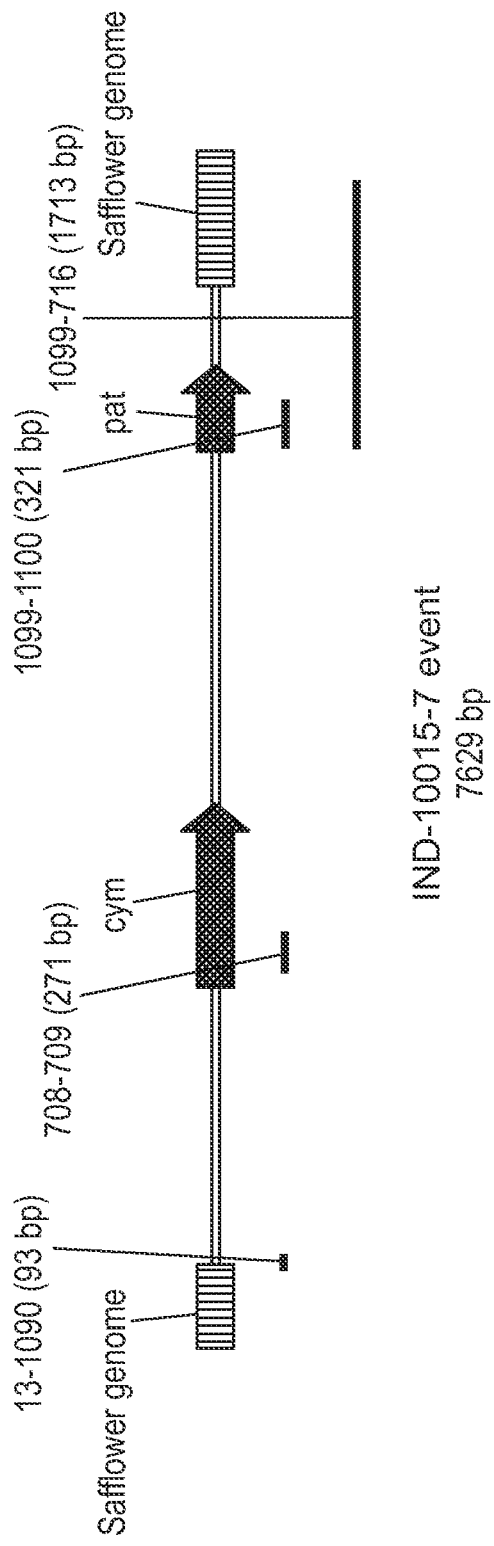
FIGS. 10A and 10B: Diagram of the elements detected in the stability analysis on the events IND-1ØØ15-7 and IND-1ØØØ3-4. Detected coding regions belonging to the T-DNA, cym and pat, in orange, and flanking sequences corresponding to the safflower genome in the two insertion events in red. The horizontal red lines indicate the amplicons obtained by PCR, and in brackets the size in base pairs (bp) and oligonucleotides used.
Figure 10B:
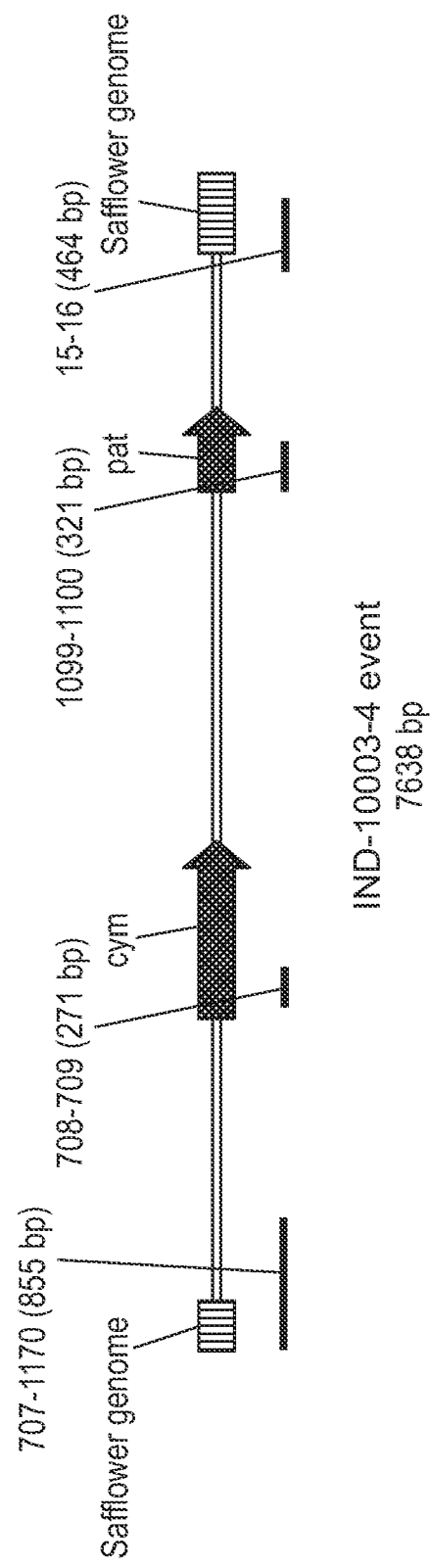

Both oligonucleotides and amplified regions are outlined in FIG. 10. They are partly the same ones used in the F2 segregation analysis, which were also used to identify homozygous individuals for both events that gave rise to F3 homozygous lines that originated the generations used in this study.

All the plants used in this analysis, 20 per generation, were homozygous for both insertion events and, therefore, all the elements analyzed were detected in them: the pat and cym coding regions and the four event-specific sequences.

Example 4: Useful Methods for Identifying IND-1ØØØ3-4×IND-1ØØ15-7 in One Sample

Molecular biology techniques involving amplification of specific DNA fragments by polymerase chain reaction (PCR) are used to identify the presence/absence of the event and the insert sites (joint points) (JP). The methodologies used, as well as the reaction mixes and amplification programs required for each determination, are detailed below.

Detection of the Insert Sites (Joint Points) (JP)

Figure 11:
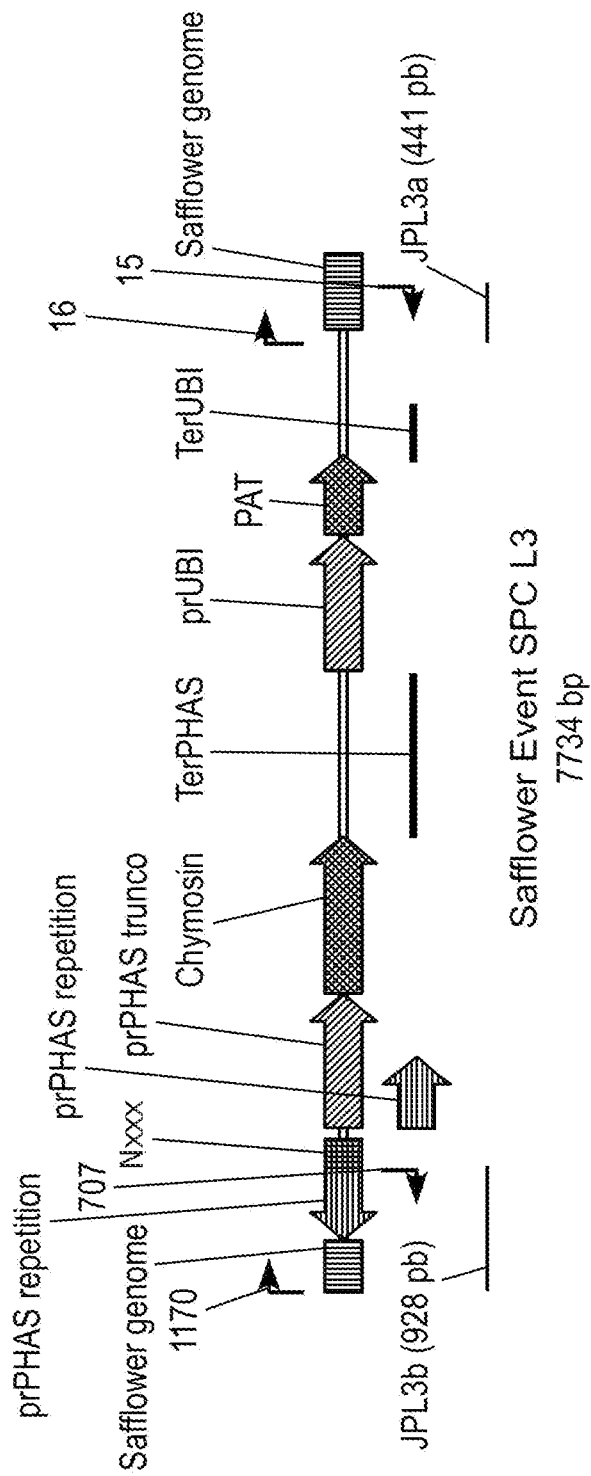
FIG. 11: Detection of the joint points (JP) of the event IND-1ØØØ3-4, left border of the T-DNA (JPL3a) and right border of the T-DNA (JPL3b). Both JPL3a and JPL3b are evaluated by end time PCR. The diagram shows the specific oligonucleotides and the sizes of the amplicons.
Figure 12:
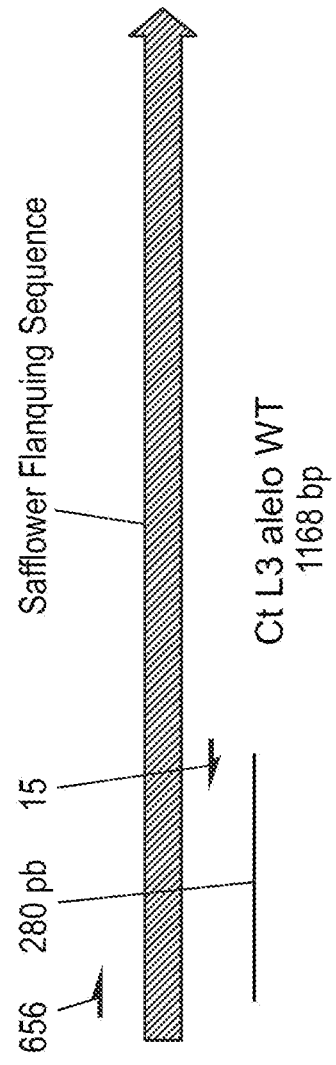
FIG. 12: Detection of the WT allele corresponding to the event IND-1ØØØ3-4. This region is evaluated by end time PCR. The specific oligonucleotides and the size of the amplicon are indicated in the diagram.

The presence of the insert site of event IND-1ØØØ3-4 is determined by the technique of end time PCR, using the primers of SEQ ID NO: 6 and 7 for the left border insert site of the T-DNA of event IND-1ØØØ3-4 (JPL3a) and the primers of SEQ ID NO: 8 and 9 for the right border insert site of the T-DNA of event IND-1ØØØ3-4 (JPL3b) (FIG. 11). The WT allele of IND-1ØØØ3-4 is also detected by end-time PCR, using the primers of SEQ ID NO: 6 and 10 (FIG. 12).

Figure 13:
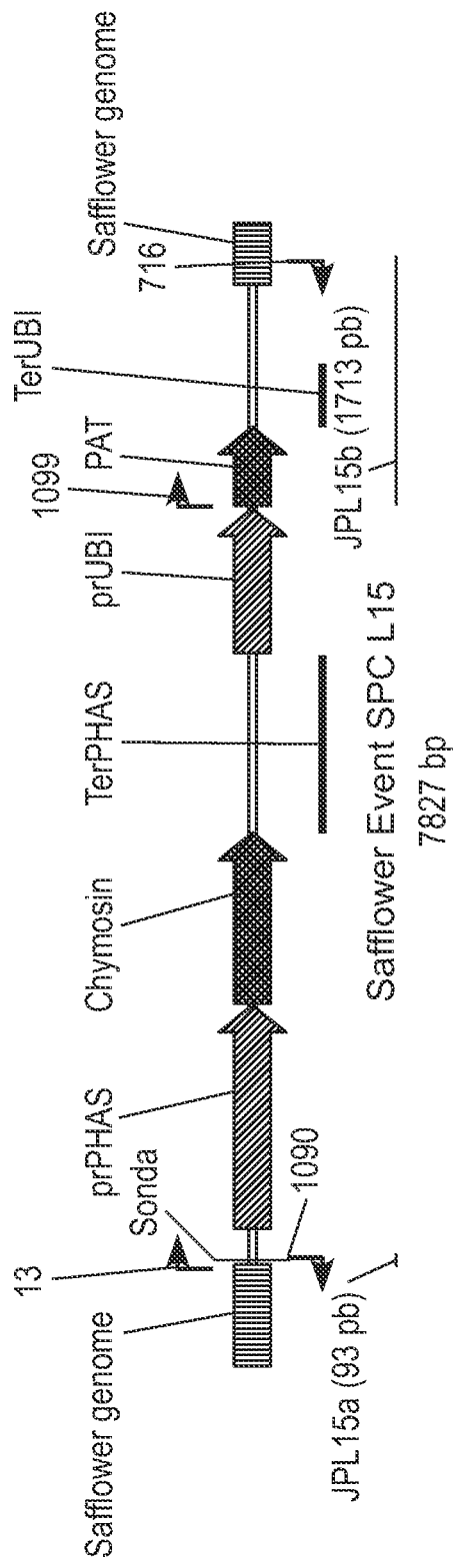
FIG. 13: Detection of the joint points (JP) of event IND-1ØØ15-7, left border of T-DNA (JPL15a) and right border of T-DNA (JPL15b). JPL15a is evaluated by qPCR and JPL15b is evaluated by end time PCR. The diagram shows the specific oligonucleotides, probe and amplicon sizes.
Figure 14:
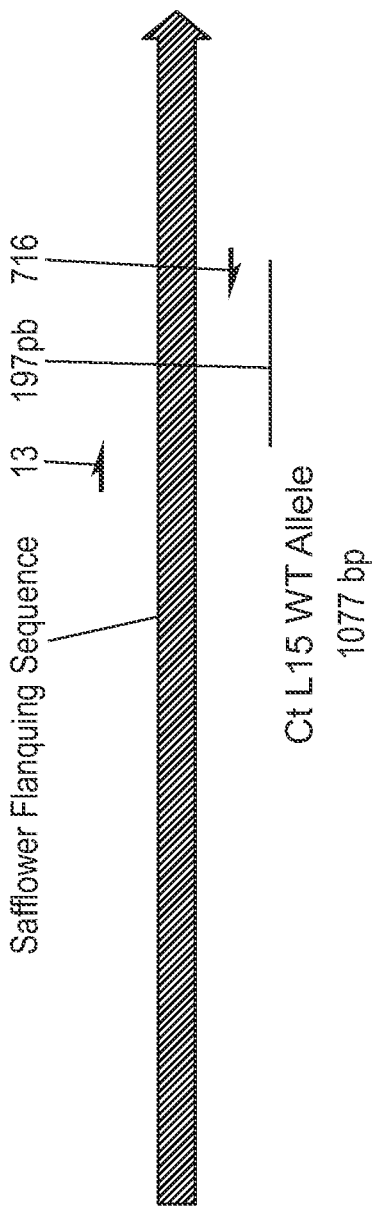
FIG. 14: Detection of the WT allele corresponding to the event IND-1ØØ15-7. This region is evaluated by end time PCR. The specific oligonucleotides and the size of the amplicon are indicated in the diagram.

As for event IND-1ØØ15-7, the detection of the insertion site of the left border of the T-DNA of the event (JPL15a) is performed by the real-time PCR technique (qPCR), using the primers of SEQ ID NO: 11 and 12 and the Taqman probe of SEQ ID NO: 13, as shown in FIG. 13. The detection of the insertion site of the right border of the T-DNA of event IND-1ØØ15-7 (JPL15b) is performed by the end-time PCR technique, using the primers of SEQ ID NO: 14 and 15 (FIG. 13). The WT allele of event IND-1ØØ15-7 is also detected by end-time PCR, using the primers of SEQ ID NO: 11 and 14 as shown in FIG. 14.

For end-time PCR, the reaction mix is used as shown in Table 2, and the amplification program in Table 3.

TABLE 2

Reaction mix End time PCR

| VOLUME | REAGENT |
|---|---|
| 2 µL | Genomic DNA (100 ng) |
| 2 µL | PCR Buffer (10×) |
| 1.6 µL | MgCl2 (25 mM) |
| 1 µL | Primer F (10 µM) |
| 1 µL | Primer R (10 µM) |
| 0.4 µL | dNTPs (10 mM) |
| 0.1 µL | Taq polymerase (5 U/µl) |

TABLE 2-continued

Reaction mix End time PCR

| VOLUME | REAGENT |
|---|---|
| 11.9 μL | mqH2O |
| 20 μL | Total reaction volume |

TABLE 3

Amplification Program

| Stage | Temperature (° C.) | Time | N° cycles |
|---|---|---|---|
| Initial Denaturing | 94° C | 240" | 1 |
| Denaturing | 94° C | 30" | 30 cycles |
| Anneal | 55° C | 30" | |
| Extention | 72° C | 30" | |
| End Reaction | 4° C. | 120" | 1 |

PCR reactions are displayed by horizontal electrophoresis on 1.5% agarose gel and sodium borate buffer. The electrophoretic run is performed at 120 V for 30 minutes.

For real-time PCR (qPCR), the reaction mix in Table 4 and the amplification program in Table 5 are used.

TABLE 4 qPCR Reaction Mix

| VOLUME | REAGENT |
|---|---|
| 2 μL | Genomic DNA (100 ng/μl) |
| 5.9 μL | (H₂O)dd |
| 10 μL | qPCRSuperMix (2×) |
| 0.5 μL | bar Probe (10 μM) |
| 0.8 μL | bar Primer F (10 μM) |
| 0.8 μL | bar Primer R (10 μM) |
| 20 μL | Total reaction volume |

TABLE 5

Amplification Program

| Temp (° C.) | Time | Temp. Ramp (° C./s) |
|---|---|---|
| 95 | 5 minutes | 4.4 |
| 95 | 15 seconds | 4.4 |
| 55 | 30 seconds | 1.8 |
| 72 | 1 second | 4.4 |
| 10 | 5 minutes | 2.2 |

By detecting one of the insertion sites for each event and the WT allele for both events, it is possible to determine the genotype of the individual; IND-1ØØØ3-4, IND-1ØØ15-7 or IND-1ØØØ3-4×IND-1ØØ15-7.

Event Detection

In order to determine event IND-1ØØØ3-4 the primers used are those of SEQ ID NO: 16 and 17, an amplicon of 108 bp is obtained, using the probe of SEQ ID NO: 18.

For event IND-1ØØ15-7 the primers used are those of SEQ ID NO: 11 and 12, and the probe of SEQ ID NO: 13, and an amplicon of 93 bp is obtained.

For these determinations, real-time PCR (qPCR), the reaction mix in Table 6 and the amplification program in Table 7 are used.

TABLE 6 qPCR Reaction Mix

| Reagent | Final Concentration | μL/reaction |
|---|---|---|
| LightCycler ® 480 Probes Master (Roche) (2×) | 1× | 5 μL |
| Direct Primer (10 μM) | 0.4 μM | 0.4 μL |
| Reverse Primer (10 μM) | 0.4 μM | 0.4 μL |
| Probe (10 μM) | 0.25 μM | 0.25 μL |
| H₂0 nuclease-free | — | 2.95 μL |
| DNA (100 ng) | — | 1 μL |
| End reaction volume | | 10 μL |

TABLE 7

Amplification Program

| Temp (° C.) | Time | Temp. Ramp (° C./s) | Number of cycles |
|---|---|---|---|
| 95 | 5 minutes | 4.4 | Denaturing |
| 95 | 15 seconds | 4.4 | |
| 55 | 30 seconds | 1.8 | 35 cycles qPCR |
| 72 | 10 seconds | 4.4 | |
| 10 | 5 minutes | 2.2 | Cooling |

Example 5: Agronomic Traits and Performance

To evaluate the agronomic traits and grain yield of molecular stacking of safflower events IND-1ØØØ3-4× IND-1ØØ15-7 trials were conducted in 3 different locations in the period of 2014/2015 as shown in Table 8. The events were planted together with a Centennial, the control of the wild type and a number of conventional varieties. The materials sown included the molecular stacking of safflower events IND-1ØØØ3-4×IND-1ØØ15-7, the untransformed control variety (Centennial) and commercial cultivars used as reference (Table 9). The trials were conducted following the usual practices of cultural management of the crop.

TABLE 8

Locations

| Site | City | Province | Type of occurrence | Planting date | Harvest date |
|---|---|---|---|---|---|
| VS | Villa Saboya | Buenos Aires | Hapludol Entico | 26 Aug. 2014 | 29 Jan. 2015 |
| BB | Bahia Blanca | Buenos Aires | Typical Haplustol | 30 Jul. 2014 | 28 Jan. 2015 |
| MC | Montecristo | Córdoba | Typical Haplustol | 7 Jul. 2014 | 21 Jan. 2015 |

TABLE 9

Entries evaluated in field trials

| Entries | Material Type |
|---|---|
| Safflower SPC_DC# | GM |
| Centennial | Control |
| S-518 | Commercial |
| S-555 | Commercial |
| 9-ECR | Experimental |
| CW88 | Commercial |
| CW99 | Commercial |

Safflower SPC_DC: IND-1ØØØ3-4 × IND-1ØØ15-7

Trial Design

The plots were sown using a randomized complete block design with four replicates. Each plot consisted of four rows spaced 0.4 meters apart (Villa Saboya) or 0.52 meters apart (Monte Cristo and Bahia Blanca) and 10 meters long. The seeds were treated with Maxim Evolution (100 cc/100 kg seed) before planting. The planting density was 40 plants m-2, approximately. The trials plots were surrounded by a four-furrow border of a commercial material (S-719). An electric fence was installed in each trial plot to prevent animals from entering the plots.

Seed increments of the transgenic event were performed in Roldan on two planting dates and in Villa Saboya. In each location, 180 m2 were planted.

The weather conditions during the growing season at each site are shown in Table 10. At each site, appropriate agrochemicals were applied both before planting and during the crop cycle to control weeds, pests and diseases (Table 11).

TABLE 10

Rainfall recorded at each site during the 2014 season

| | Rainfall (mm) | | | | | |
|---|---|---|---|---|---|---|
| | 2014 | | | 2015 | | |
| Site | August | September | October | November | December | January | Total |
| VS | 0 | 48 | 71 | 51 | 97 | 195 | 462 |
| BB | 95 | 58 | 165 | 101 | 48 | 86 | 553 |
| MC | — | 9 | 51 | 39 | 52 | 125 | 276 |

TABLE 11

Agrochemicals used to control weeds, pests and diseases during the 2014 season at each site

| Date | Site | Rate of application | Product (Commercial name) | Purpose |
|---|---|---|---|---|
| 26 Aug. 2014 | VS | 3 L ha − 1 | GlyPhosate (Roundup Full II) | Pre-Planting herbicide |
| 21 Nov. 2014 | VS | 0.5 L ha − 1 | Azoxystrobin + Ciproconazole (Amistar xtra) | Fungicide |
| 21 Nov. 2014 | VS | 0.5 L ha − 1 | Clorpirifós (Nurfam) | Insecticide |
| 21 Nov. 2014 | VS | 0.125 L ha − 1 | Alfacipermetrina (Fastac 10) | Insecticide |
| 7 Jul. 2014 | MC | 100 Kg ha − 1 | Fosfato Monoamonico | Fertilizer |
| 14 Nov. 2014 | MC | 0.5 L ha − 1 | Azoxystrobin + Tebuconazole (Custodia) | Fungicide |
| 14 Nov. 2014 | MC | 0.25 L ha − 1 | Imidacloprid (Matrero 35) | Insecticide |
| 12 Dec. 2014 | MC | 0.5 L ha − 1 | Azoxystrobin + Tebuconazole (Custodia) | Fungicide |
| 23 Jul. 2014 | BB | 2.5 Kg ha − 1 | Gliphosate (Round Up Ultramax) | Pre-Planting herbicide |
| 20 Nov. 2014 | BB | 0.5 L ha − 1 | Azoxystrobin + Ciproconazole (Amistar xtra) | Fungicide |
| 20 Nov. 2014 | BB | 0.5 L ha − 1 | Clorpirifós (Nurfam) | Insecticide |
| 20 Nov. 2014 | BB | 0.125 L ha − 1 | Alfacipermetrina (Fastac 10) | Insecticide |
| 16 Jan. 2015 | BB | 1.5 Kg ha − 1 | Gliphosate (Round Up Ultramax) | Drying |
| 16 Jan. 2015 | BB | 0.5 L ha − 1 | Clorpirifós (Nurfam) | Insecticide |
| 16 Jan. 2015 | BB | 0.2 L ha − 1 | Imidacloprid (Confidor 350SC) | Insecticide |

VS: Villa Saboya; MC: Monte Cristo, BB: Bahía Blanca

Data Collection

The data collected in the trials include days to emergence, seedling vigor, initial and final stand of plants, phenology, plant height at two points in the cycle, lodging, grain moisture at harvest and yield (Table 12).

Samples were collected from different tissues at different times for analyses of protein expression and feed and grain composition (Table 12). The tissues used to measure the expression of the expressed proteins were preserved at −20° C., except for the grain, which was kept at room temperature for, further compositional analysis. The plants collected for fodder composition determinations were dried in an oven for 2 or 3 days at 50-60° C. and preserved in a fresh and dry place, for its later transfer to the laboratory specialized in compositional analysis.

TABLE 12

List of agronomic parameters measured

| Trait | Scale |
|---|---|
| Days to emergence (days) | Date recorded when 50% of plants in each plot were emerging. Days since planting calculated |
| Early and final plant stand (plants · m − 1) | Emerged plants in 1 meter is calculated by the total number of plants of the two central rows divided by the row's length |
| Seedling vigour (1-9 scale) | 1-3: 3 cm of diameter rosette, small leaves, low development and pale green colour, very low or low vigour. |
| | 4-6: 10 cm of diameter rosette, average leaf size, deep green colour, medium vigour. |
| | 7-9: mor than 10 cm of diameter rosette, large leaves, very deep green colour, and high vigour. |
| Days to stem elongation (days) | Date recorded when 50% of plants in each plot were stem elongation. Days since planting calculated |
| Days to floral bud (days) | Date recorded when 50% of plants in each plot were floral bud. Days since planting calculated |
| Plant height (cm) on floral bud | Recorded the average height of five representative plants of each plot on floral bud |
| Days to flowering (days) | Date recorded when 50% of plants in each plot were flowering. Days since planting calculated |
| Days to maturity (days) | Date recorded when 50% of plants in each plot reach maturity. Days since planting calculated |

TABLE 12

List of agronomic parameters measured (cont.)

| Trait | Scale |
|---|---|
| Lodging Score (1-9) | 1 more than 90% of plant lying flat; |
| | 2-3 more than 75% of plants lying flat; |
| | 4-5 more than 50% of plants lying flat; |

TABLE 12-continued

List of agronomic parameters measured (cont.)

| Trait | Scale |
|---|---|
| | 6-7 more than 25% of plants lying flat; 8 less than 10% of plants lying flat 9 all plants erect |
| Plant height (cm) to maturity | Recorded the average height of five representative plants of each plot to maturity |
| Final plant stand (plants · m − 1) | Emerged plants in 1 meter is calculated by the total number of plants of the two central rows divided by the row's length |
| Grain moisture (%) | Moisture (%) of a sample from bulk yield |
| Yield (Kg · ha − 1) | Recorded the weight in grams of grain harvested from the two middle rows of each plot. Yield (Kg/ha) calculated |
| Disease damage (1-9 scale) | 1-9 Rating score; 0 None, no symptoms observed; 1-3 Mild, very little disease injury (<10%) visible; 4-6 Moderate, noticeable plant tissue damage (10%-30%); 7-9 Severe, significant plant tissue damage (>30%) |

TABLE 12

List of agronomic parameters measured (cont.)

| Trait | Scale |
|---|---|
| Insect damage (0-5) | 0-5 Rating score; 0 None, no symptoms observed; 1 (1-20%) slight, symptoms not damaging to plant development; 2 (21-40%) and 3 (41-60%) moderate (intermediate between slight and severe); 4 (61-80%) and 5 (>80%) severe (symptoms damaging to plant development) |
| Tissue sampling for protein expression | Estadio roseta: hoja Estadio cosecha: grano |
| Forage sampling for compositional analysis | Aerial biomass sampling Grain sampling at harvest |

Statistical Analysis

For each site, the transgenic event and control data were analyzed by ANOVA using the inputs and blocks as fixed factors and a significance level of 95% (p=0.05). The values from the commercial varieties were used to define the reference range. In addition, a combined analysis involving genotype interaction by environment was performed.

Disease and insect damage data were analyzed by environment/site given the natural variation that exists between sites regarding these variables.

Results

Statistical analysis revealed that there was no environmental genotype interaction for any of the traits evaluated, except for grain moisture (p=0.0044, Table 13). When the sites were analyzed separately (Tables 14, 15 and 16), both in Villa Saboya and in Bahia Blanca grain moisture was higher for the transgenic event. In Villa Saboya, the grain moisture values are within the range observed in commercial varieties, while in Bahia Blanca, the moisture value is 0.3 higher than the upper range observed for the varieties. Although this value is higher than the range for that location, the difference can be considered as biologically negligible. On the other hand, in the combined site analysis the grain moisture values for the event are within the reference ranges.

For the analysis of individual sites, in addition to the moisture differences discussed in the previous paragraph, significant differences were observed in plant height at maturity for Monte Cristo. The transgenic event showed a higher plant height (5.2 cm) with respect to the control. However, the height values observed at that location are within the range observed in the references.

With respect to ecological interactions, no significant differences in insect damage and disease were observed in any of the locations (Table 17, 18 and 19).

TABLE 13

Phenotypic traits Combined site

| Phenotypic Characteristic (units) | Mean (stándar error) IND-1ØØØ3-4 × IND-1ØØ15-7 | Centennial | Reference range |
|---|---|---|---|
| Days to emergence (days) | 17.8 ± 2.3 | 19.9 ± 2.6 | 10.3 – 27.5 |
| Seedling vigour (1-9 scale) | 2.1 ± 0.3 | 2.0 ± 0.3 | 1.0 – 6.5 |
| Early plant stand (plants · 2 m − 1) | 33.8 ± 2.8 | 29.7 ± 1.8 | 22.8 – 43.5 |
| Days to stem elongation (days) | 67.4 ± 3.6 | 66.5 ± 4.2 | 46.5 – 82.8 |
| Days to floral bud (days) | 115.9 ± 6.4 | 114.8 ± 6.3 | 82.5 – 133.5 |
| Plant height (cm) in floral bud | 62.4 ± 1.6 | 59.0 ± 2.8 | 45.0 – 75.4 |
| Days to flowering (days) | 123.1 ± 8.5 | 121.1 ± 7.8 | 98.0 – 146.8 |
| Days to maturity (days) | 150.0 ± 5.2 | 150.3 ± 4.9 | 124.5 – 170.5 |
| Lodging Score (1-9) | 9.0 ± 0.0 | 8.8 ± 0.1 | 7.0 – 9.0 |
| Plant height (cm) to maturity | 65.3 ± 1.1 | 66.8 ± 2.3 | 60.3 – 83.5 |
| Final plant stand (plants · m − 1) | 26.3 ± 1.6 | 23.1 ± 1.4 | 17.0 – 44.0 |
| Grain moisture (%) | 9.5 ± 0.5 | 8.7 ± 0.3 | * 7.8 – 15.1 |
| Yield (Kg · ha − 1) | 1222.3 ± 61.7 | 1321.8 ± 120.5 | 965.4 – 2045.1 |

* Significant differences (p < 0.05)

TABLE 14

Phenotypic traits. Villa Saboya

| Phenotypic Characteristic (units) | Mean (stándar error) IND-1ØØØ3-4 × IND-1ØØ15-7 | Centennial | Reference range |
|---|---|---|---|
| Days to emergence (days) | 12.0 ± 0.4 | 13.0 ± 0.4 | 10.3 – 12.8 |
| Seedling vigour (1-9 scale) | 2.5 ± 0.3 | 2.3 ± 0.5 | 2.3 – 5.0 |
| Early plant stand (plants · 2 m − 1) | 37.3 ± 2.7 | 35.8 ± 1.3 | 26.3 – 43.5 |
| Days to stem elongation (days) | 51.8 ± 0.5 | 48.3 ± 1.4 | 46.5 – 78.5 |
| Days to floral bud (days) | 86.0 ± 0.0 | 85.3 ± 0.8 | 82.5 – 85.3 |
| Plant height (cm) in floral bud | 64.0 ± 2.8 | 66.1 ± 1.2 | 63.2 – 75.4 |
| Days to flowering (days) | 100.8 ± 0.8 | 100.5 ± 1.4 | 98.0 – 102.3 |
| Days to maturity (days) | 127.8 ± 1.8 | 129.3 ± 0.6 | 124.5 – 127.8 |
| Lodging Score (1-9) | 9.0 ± 0.0 | 9.0 ± 0.0 | 9.0 – 9.0 |
| Plant height (cm) to maturity | 62.9 ± 0.9 | 69.0 ± 1.9 | 60.3 – 70.7 |
| Final plant stand (plants · m − 1) | 22.5 ± 1.8 | 24.5 ± 2.3 | 27.0 – 30.0 |
| Grain moisture (%) | 8.6 ± 0.1 | 8.2 ± 0.1 | * 8.0 – 8.3 |

TABLE 14-continued

Phenotypic traits. Villa Saboya

| Phenotypic Characteristic (units) | Mean (stándar error) IND-10003-4 × IND-10015-7 | Centennial | Reference range |
|---|---|---|---|
| Yield (Kg · ha − 1) | 1295.0 ± 133.2 | 1613.4 ± 210.9 | 1499.4 – 2045.1 |

* Significant differences ($p < 0.05$)

TABLE 15

Phenotypic traits. Montecristo

| Phenotypic Characteristic (units) | Mean (stándar error) IND-10003-4 × IND-10015-7 | Centennial | Reference range |
|---|---|---|---|
| Days to emergence (days) | — ± — | — ± — | — – — |
| Seedling vigour (1-9 scale) | 2.8 ± 0.8 | 2.8 ± 0.8 | 3.5 – 6.5 |
| Early plant stand (plants · 2 m − 1) | 32.6 ± 2.2 | 25.3 ± 2.7 | 36.8 – 42.3 |
| Days to stem elongation (days) | 71.8 ± 0.3 | 75.0 ± 1.8 | 68.0 – 70.0 |
| Days to floral bud (days) | 129.3 ± 1.2 | 129.5 ± 2.3 | 126.0 – 130.8 |
| Plant height (cm) in floral bud | 65.7 ± 1.8 | 61.0 ± 4.7 | 59.0 – 70.8 |
| Days to flowering (days) | — ± — | — ± — | — – — |
| Days to maturity (days) | 169.3 ± 0.5 | 168.5 ± 0.9 | 168.0 – 170.5 |
| Lodging Score (1-9) | 9.0 ± 0.0 | 8.5 ± 0.3 | 7.0 – 7.5 |
| Plant height (cm) to maturity | 67.7 ± 2.5 | 62.5 ± 2.7 | * 61.3 – 72.3 |
| Final plant stand (plants · m − 1) | 30.8 ± 2.3 | 24.8 ± 2.8 | 35.3 – 40.5 |
| Grain moisture (%) | 8.3 ± 0.1 | 8.1 ± 0.1 | 7.8 – 8.4 |
| Yield (Kg · ha − 1) | 1149.7 ± 73.3 | 1030.2 ± 21.1 | 965.4 – 1404.8 |

* Significant differences ($p < 0.05$)

TABLE 16

Phenotypic traits. Bahía Blanca

| Phenotypic Characteristic (units) | Mean (stándar error) IND-10003-4 × IND-10015-7 | Centennial | Reference range |
|---|---|---|---|
| Days to emergence (days) | 21.0 ± 1.4 | 26.0 ± 0.8 | 17.0 – 27.5 |
| Seedling vigour (1-9 scale) | 1.0 ± 0.0 | 1.0 ± 0.0 | 1.0 – 4.0 |
| Early plant stand (plants · 2 m − 1) | 32.0 ± 8.4 | 28.0 ± 2.8 | 22.8 – 37.3 |
| Days to stem elongation (days) | 78.8 ± 3.3 | 76.3 ± 4.2 | 69.0 – 82.8 |
| Days to floral bud (days) | 132.5 ± 1.5 | 129.5 ± 1.5 | 128.0 – 133.5 |
| Plant height (cm) in floral bud | 57.5 ± 2.5 | 50.0 ± 4.1 | 45.0 – 67.5 |
| Days to flowering (days) | 145.5 ± 2.5 | 141.8 ± 1.3 | 134.0 – 146.8 |
| Days to maturity (days) | 153.0 ± 0.0 | 153.0 ± 0.0 | 148.0 – 153.0 |
| Lodging Score (1-9) | 9.0 ± 0.0 | 9.0 ± 0.0 | 9.0 – 9.0 |
| Plant height (cm) to maturity | 65.3 ± 1.6 | 68.0 ± 5.9 | 65.4 – 83.5 |
| Final plant stand (plants · m − 1) | 20.0 ± 2.3 | 25.8 ± 3.0 | 17.0 – 44.0 |
| Grain moisture (%) | 11.6 ± 0.6 | 9.8 ± 0.3 | * 8.0 – 15.1 |
| Yield (Kg · ha − 1) | — ± — | — ± — | — – — |

* Significant differences ($p < 0.05$)

TABLE 17

Disease and insect damage. Villa Saboya

| Damage agent | Phenological stages | Mean (stándar error) IND-10003-4 × IND-10015-7 | Centennial | Reference range |
|---|---|---|---|---|
| Deseases | VRn | 0.0 ± 0.0 | 0.0 ± 0.0 | 0.0 – 0.0 |
| Insects | VRn | 0.0 ± 0.0 | 0.0 ± 0.0 | 0.0 – 0.0 |
| Deseases | BT | 3.0 ± 0.4 | 3.0 ± 0.4 | 2.0 – 0.6 |
| Insects | BT | 1.0 ± 0.0 | 1.0 ± 0.0 | 1.0 – 1.0 |
| Deseases | FL | 0.5 ± 0.5 | 0.0 ± 0.0 | 0.0 – 0.8 |
| Insects | FL | 0.0 ± 0.0 | 0.0 ± 0.0 | 0.0 – 0.0 |
| Insects | MF | 1.0 ± 0.0 | 1.0 ± 0.0 | 1.0 – 1.0 |

VRn: rosette; BT: floral bud; FL: flowering; MF: physiological mature

TABLE 18

Disease and insect damage. Montecristo

| Damage agent | Phenological stages | Mean (stándar error) IND-10003-4 × IND-10015-7 | Centennial | Reference range |
|---|---|---|---|---|
| Deseases | VRn | 0.0 ± 0.0 | 0.0 ± 0.0 | 0.0 – 0.0 |
| Insects | VRn | 0.0 ± 0.0 | 0.0 ± 0.0 | 0.0 – 0.0 |
| Deseases | BT | 1.5 ± 0.3 | 1.0 ± 0.0 | 1.0 – 1.5 |
| Insects | BT | 0.3 ± 0.3 | 0.5 ± 0.3 | 0.0 – 0.8 |
| Deseases | FL | 1.8 ± 0.3 | 2.0 ± 0.0 | 1.3 – 1.8 |
| Insects | FL | 0.0 ± 0.0 | 0.0 ± 0.0 | 0.0 – 0.0 |
| Insects | ET | 0.0 ± 0.0 | 0.0 ± 0.0 | 0.0 – 0.0 |

VRn: rosette; BT: floral bud; FL: flowering; MF: physiological mature

TABLE 19

Disease and insect damage. Bahía Blanca

| Damage agent | Phenological stages | Mean (stándar error) IND-10003-4 × IND-10015-7 | Centennial | Reference range |
|---|---|---|---|---|
| Deseases | VRn | 0.0 ± 0.0 | 0.0 ± 0.0 | 0.0 – 0.0 |
| Insects | VRn | 0.0 ± 0.0 | 0.0 ± 0.0 | 0.0 – 0.0 |
| Deseases | BT | 0.0 ± 0.0 | 0.0 ± 0.0 | 0.0 – 0.0 |
| Insects | BT | 0.0 ± 0.0 | 0.0 ± 0.0 | 0.0 – 0.0 |
| Deseases | FL | 0.0 ± 0.0 | 0.0 ± 0.0 | 0.0 – 0.0 |

TABLE 19-continued

Disease and insect damage. Bahía Blanca

| Damage agent | Phenological stages | Mean (stándar error) | | Reference range |
|---|---|---|---|---|
| | | IND-1ØØØ3-4 × IND-1ØØ15-7 | Centennial | |
| Insects | FL | 0.0 ± 0.0 | 0.0 ± 0.0 | 0.0 – 0.0 |
| Insects | ET | 0.0 ± 0.0 | 0.0 ± 0.0 | 0.0 – 0.0 |

VRn: rosette; BT: floral bud; FL: flowering; ET: stem elongation; MF: physiological mature

CONCLUSIONS

The results presented of the agronomic traits and the interaction of the molecular stack of safflower events with the environment confirm the agronomic equivalence of the transgenic event with the control and with the commercial varieties grown in parallel. Therefore, no adverse effects are expected from the presence of IND-1ØØØ3-4×IND-1ØØ15-7 or the use of varieties derived from it, while molecular stacking of safflower events results in higher levels of chymosin expression.

Having especially described and determined the nature of the present invention and having explained how to implement it, we claim the exclusive property right on:

1. A safflower transgenic plant or part thereof, wherein the genome of the transgenic plant or part thereof comprises the sequence SEQ ID NO: 1 and the sequence SEQ ID NO: 2, and wherein the safflower transgenic plant produces at least 2 mg of bovine chymosin/g of seeds.

2. A safflower transgenic plant seed in accordance with claim 1, comprising SEQ ID NO: 1 and SEQ ID NO: 2.

3. The part of the safflower transgenic plant according to claim 1, defined as a cell, pollen, egg, flower, seed, shoot, root or leaf.

4. A safflower progeny plant of the safflower transgenic plant, or a part thereof according to claim 1, wherein the genome of the progeny plant comprises the sequence SEQ ID NO: 1 and the sequence SEQ ID NO: 2.

5. An expression vector comprising a recombinant DNA molecule that comprises the sequence SEQ ID NO: 7.

* * * * *